United States Patent [19]
Dodey et al.

[11] Patent Number: 6,071,917
[45] Date of Patent: Jun. 6, 2000

[54] N-BENZENESULPHONYL-L-PROLINE DERIVATIVES AS BRADYKININ $B_2$ ANTAGONISTS

[75] Inventors: Pierre Dodey; Michel Bondoux, both of Fontaine-lès-Dijon; Patrick Houziaux, Bazemont; Martine Barth, Montfort-l'Amaury; Khan Ou, Hauteville-lès-Dijon, all of France

[73] Assignee: Fournier Industrie Et Sante, France

[21] Appl. No.: 09/230,334

[22] PCT Filed: Jul. 23, 1997

[86] PCT No.: PCT/FR97/01377

§ 371 Date: Jan. 25, 1999

§ 102(e) Date: Jan. 25, 1999

[87] PCT Pub. No.: WO98/03503

PCT Pub. Date: Jan. 29, 1998

[30] Foreign Application Priority Data

Jul. 24, 1996 [FR] France .................................. 96 09327

[51] Int. Cl.⁷ ........................ A61K 31/47; A61K 31/495; C07D 401/12; C07D 401/14; C07D 403/14
[52] U.S. Cl. .................... 514/253; 514/218; 514/314; 540/575; 544/363; 546/172
[58] Field of Search .................... 546/172; 514/314, 514/253, 218; 544/363; 540/575

[56] References Cited

FOREIGN PATENT DOCUMENTS

| | | |
|---|---|---|
| 0 261 539 | 3/1988 | European Pat. Off. . |
| 0 596 406 A1 | 5/1994 | European Pat. Off. . |
| 0 622 361 | 11/1994 | European Pat. Off. . |
| 36 17 183 A1 | 5/1987 | Germany . |
| WO 96/13485 | 5/1996 | WIPO . |
| WO 96/40639 | 12/1996 | WIPO . |
| WO 97/07115 | 2/1997 | WIPO . |
| WO 97/24349 | 7/1997 | WIPO . |

OTHER PUBLICATIONS

Stewart JM. Biopolymers (Peptide Science). 37, 143–155 1995.
Stewart JM. Recent Progress on Kinins. Birkhauser Verlag Basel. pp.546–550 1992.

*Primary Examiner*—Evelyn Mei Huang
*Attorney, Agent, or Firm*—Evenson, McKeown, Edwards & Lenahan, P.L.L.C.

[57] ABSTRACT

Compounds selected from the group which consists of the compounds of formula (I),

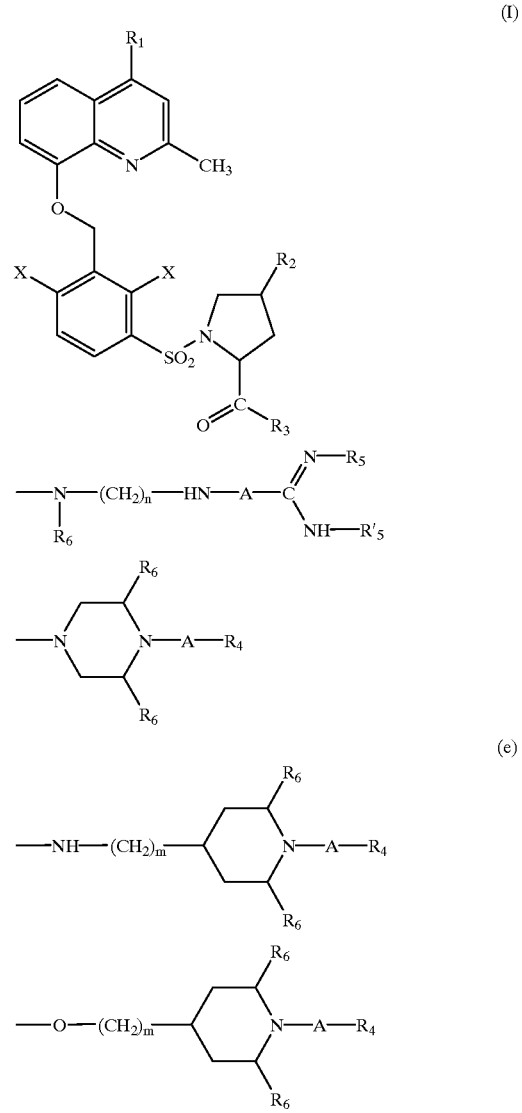

wherein each of $X_1$ and $X_2$ which are the same or different, is halogen or a $C_{1-3}$ alkoxy group, $R_1$ is H, $CF_3$ or a $C_{1-3}$ alkyl group, $R_2$ is a hydrogen atom or an OH group, A is group (a), (b) or (c), B is a single bond, —CO—, —CO—$CH_2$—, —CO—$CH_2$—O—, —CO—CH=CH or —$SO_2$—, m is 2 or 3, N is 0, 1, 2 or 3, $R_3$ is a hydrogen atom or a methyl group and W is CH or N, the amidine group C(=$NR_2$)$NH_2$ being in the 2, 3 or 4 position on the aromatic ring, and addition salts thereof, are disclosed. A method for preparing said compounds, and the therapeutical use thereof, particularly for treating diseases in which bradykinin is involved, are also disclosed.

17 Claims, No Drawings

N-BENZENESULPHONYL-L-PROLINE DERIVATIVES AS BRADYKININ B₂ ANTAGONISTS

This application is the national phase of PCT/FR97/01377 filed on Jul. 23, 1997.

FIELD OF THE INVENTION

The present invention relates to novel compounds derived from N-benzenesulfonyl-L-proline, to the process for their preparation and to their use in therapeutics.

These novel compounds have an inhibitory action on bradykinin and are useful in therapeutics, particularly for the treatment of pain and inflammation and especially for the treatment of asthma, cerebral traumatic shock and allergic rhinitis.

PRIOR ART

It is known that one of the possible treatments for certain pathological conditions of a painful and/or inflammatory nature (such as asthma, rhinitis, septic shock, toothache, etc.) is to inhibit the action of certain hormones such as bradykinin or kallidin. These peptide hormones are in fact involved in a large number of physiological processes, some of which are closely associated with these pathological conditions.

Although no product possessing this mode of action has yet been marketed, numerous studies have been undertaken to create compounds capable of antagonizing the bradykinin receptors. Bradykinin is a peptide hormone consisting of 9 amino acids (Arg-Pro-Pro-Gly-Phe-Ser-Pro-Phe-Arg (SEQ ID NO:1)) and kallidin is a peptide hormone (Lys-Arg-Pro-Pro-Gly-Phe-Ser-Pro-Phe-Arg (SEQ ID NO:2)) which contains an additional amino acid (Lys) compared with bradykinin. It is known that earlier studies made it possible to obtain peptides which interact with the bradykinin receptors: some of them, like bradycor (CP.0127 from Cortech), icatibant (FHOE 140 from Hoechst) ["bradycor" and "icatibant" are international non-proprietary names (INN)] or NPC 17761 (from Scios-Nova), have an inhibitory action on the binding of bradykinin to its B₂ receptor. More recently, non-peptide compounds have been proposed as antagonists towards the binding of bradykinin to its B₂ receptor, especially in EP-A-0596406 and EP-A-0622361. It is also known that certain compounds whose structure is related to those of the compounds referred to in the two patent applications cited above have already been described for their possible antithrombotic properties, especially in DE-A-3617183 and EP-A-0261539.

OBJECT OF THE INVENTION

There is a need for reducing or eliminating pain and inflammation in mammals and particularly in man.

To meet this need, a novel technical solution has been sought which is effective in the treatment of inflammation and pain, irrespective of their origin, and especially in the treatment of pain associated with inflammatory phenomena.

According to the invention, it is proposed to provide a novel technical solution which involves competitive binding, at the bradykinin B₂ receptor, between (i) bradykinin and related or analogous hormones, and (ii) an antagonist, and utilizes benzenesulfonamide compounds which are structurally different from the known products mentioned above and which limit or substantially inhibit the binding of bradykinin and analogous hormones to said bradykinin B₂ receptor.

In accordance with this novel technical solution, it is proposed according to a first aspect of the invention to provide compounds derived from N-benzenesulfonyl-L-proline as novel industrial products, according to a second aspect of the invention to provide a process for the preparation of these compounds, and according to a third aspect of the invention to provide the use of these compounds, especially in therapeutics, as analgesics and/or anti-inflammatories.

SUBJECT OF THE INVENTION

In accordance with the novel technical solution of the invention, a compound derived from N-benzenesulfonyl-L-proline is recommended as a novel industrial product, said compound being characterized in that it is selected from the group consisting of:

(i) the compounds of the formula

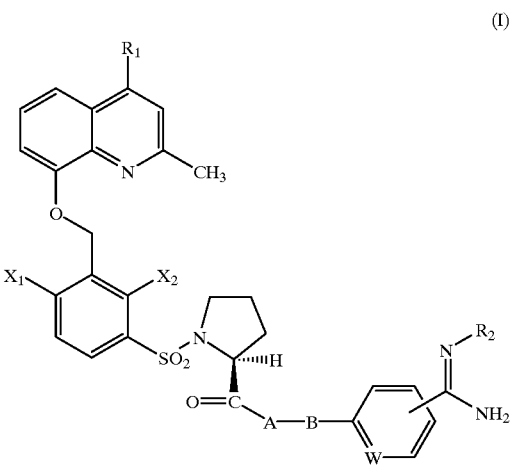

in which:
- X₁ and X₂ are each independently a halogen atom or a C₁–C₃-alkoxy group,
- R₁ is a hydrogen atom, a C₁–C₃-trifluoroalkyl group or a C₁–C₃-alkyl group with a linear or branched hydrocarbon chain,
- R₂ is a hydrogen atom or an OH group,
- A is a group

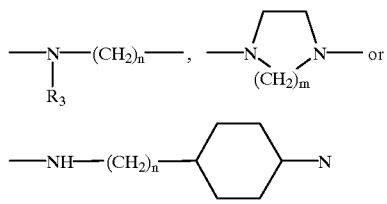

- B is a single bond, —CO—, —CO—CH₂—, —CO—CH₂—O—, —CO—CH=CH— or —SO₂—,
- m is 2 or 3,
- n is 0, 1, 2 or 3,
- R₃ is a hydrogen atom or a methyl group,
- W is CH (the aromatic ring is the phenyl group) or N (the aromatic ring is a pyridyl group), and
- the amidine group C(=NR₂)NH₂ can be in the 2-, 3- or 4-position on the aromatic ring; and (ii) their addition salts.

According to the invention, a process for the preparation of the compounds of formula I and their addition salts is also recommended.

The use of a substance which antagonizes a receptor of bradykinin and analogous hormones is also recommended, said use being characterized in that a bradykinin $B_2$ receptor antagonist selected from the compounds of formula I and their non-toxic addition salts is employed for obtaining a drug intended for use in therapeutics to combat pathological conditions involving bradykinin or its analogs, in particular to combat pain, and especially in the treatment or prevention of pathological conditions associated with inflammatory or painful states.

DETAILED DESCRIPTION OF THE INVENTION

In general formula I of the compounds of the invention, halogen atom is understood as meaning a fluorine, chlorine, bromine or iodine atom, the preferred halogen being the chlorine atom.

$C_1$–$C_3$-alkyl group with a linear or branched hydrocarbon chain is understood here as meaning a methyl, ethyl, propyl or 1-methylethyl group.

In the compound of formula I, the nitrogen heterocycle of pyrrolidine structure comprises 1 asymmetric carbon atom. According to the invention, this carbon has the S configuration, which corresponds to the configuration of L-proline.

"Addition salts" are understood as meaning the acid addition salts obtained by reacting a compound of formula I with a mineral acid or an organic acid. The preferred mineral acids for salifying a basic compound of formula I are hydrochloric, hydrobromic, phosphoric and sulfuric acids. The preferred organic acids for salifying a basic compound of formula I are methanesulfonic, benzenesulfonic, maleic, fumaric, oxalic, citric, lactic and trifluoroacetic acids.

The process recommended according to the invention for the preparation of the compounds of formula I comprises, according to a first variant A, the steps which consist in:
(1°) reacting an acid of the formula (II)

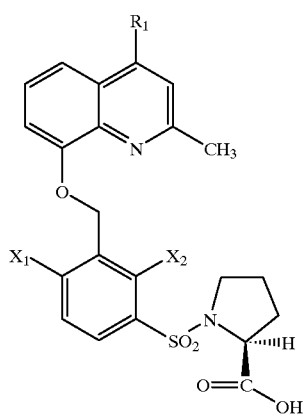

in which:
R$_1$ is a hydrogen atom, a trifluoromethyl group or a C$_1$–C$_3$-alkyl group with a linear or branched hydrocarbon chain, and
X$_1$ and X$_2$ are each independently a halogen or a C$_1$–C$_3$-alkoxy group, with an amine of the formula (III)

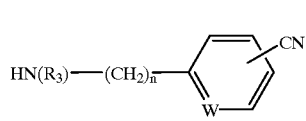

in which R$_3$ is a hydrogen atom or a methyl group, n is 0, 1, 2 or 3, and W is CH or N, in a solvent, for example dichloromethane, in the presence of activators commonly used to create bonds of the peptide type, for example 1-(3-dimethylaminopropyl)-3-ethylcarbodiimide hydrochloride (EDCI) and 1-hydroxy-7-azabenzotriazole (HOAT), at a temperature close to room temperature (i.e. a temperature between about 0 and about 40° C. and preferably a temperature between 10 and 35° C.), for 2 to 50 hours, to give a compound of the formula (IV)

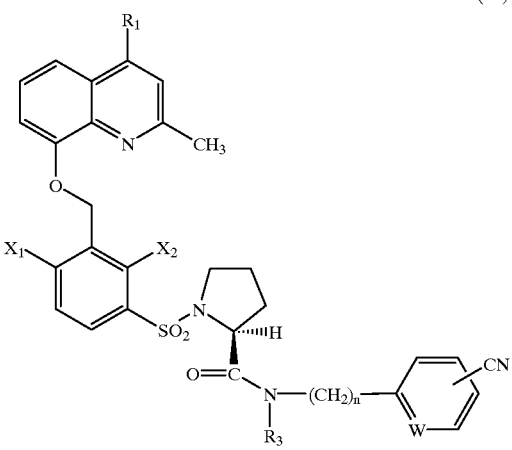

in which R$_1$, R$_3$, X$_1$, X$_2$, n and W are as defined above;
(2°) reacting the resulting compound of formula IV with excess hydrogen sulfide, in an anhydrous solvent of the pyridine type, in the presence of triethylamine, at a temperature between 0 and 40° C., for 2 to 40 hours, to give a compound of the formula (V)

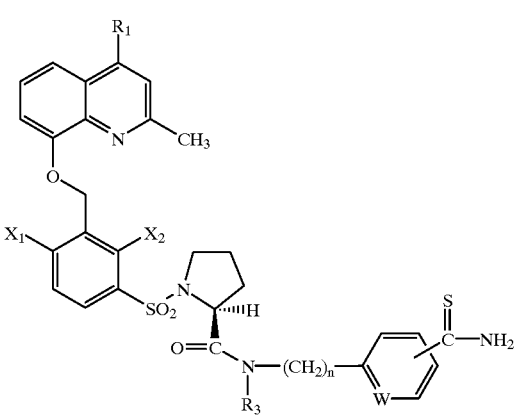

in which R$_1$, R$_3$, X$_1$, X$_2$, n and W are as defined above;
3°) reacting the resulting compound of formula V with an excess of a methylating agent, preferably methyl iodide, in a solvent, for example acetone, at a temperature close to the boiling point of the reaction medium, optionally under a pressure above atmospheric pressure, for 1 to 5 hours, to give a compound of the formula

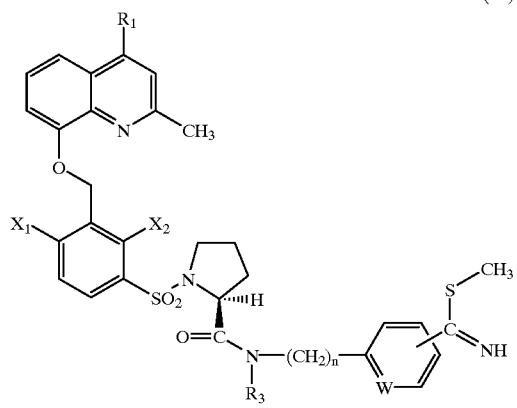

(VI)

or one of its addition salts,
in which $R_1$, $R_3$, $X_1$, $X_2$, n and W are as defined above;
(4°) reacting the resulting compound of formula VI with an ammonium salt, preferably ammonium acetate, in a solvent, for example ethanol, at a temperature between room temperature and 100° C., for 1 to 10 hours, to give a compound of formula I:

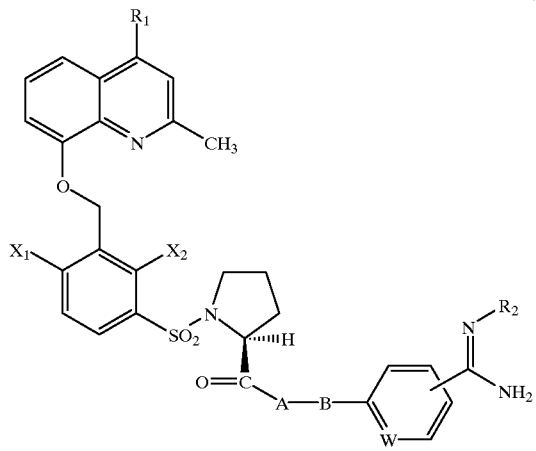

(I)

in which:
$R_1$ is a hydrogen atom, a trifluoromethyl group or a $C_1$–$C_3$-alkyl group with a linear or branched hydrocarbon chain,
$X_1$ and $X_2$ are each independently a halogen atom or a $C_1$–$C_3$-alkoxy group,
A is a group —N($R_3$)—($CH_2$)$_n$—,
B is a single bond,
W is CH or N,
$R_2$ is a hydrogen atom,
$R_3$ is H or $CH_3$, and
n is 0, 1, 2 or 3; and
(5°) if necessary, reacting the resulting compound of formula I, in the form of the free base, with a mineral or organic acid to give the corresponding acid addition salt; or according to a second variant B, the steps which consist in:

(1°) reacting a compound of the formula

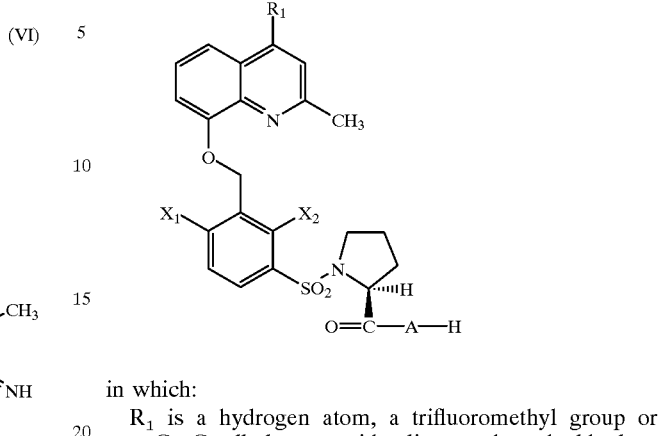

(VII)

in which:
$R_1$ is a hydrogen atom, a trifluoromethyl group or a $C_1$–$C_3$-alkyl group with a linear or branched hydrocarbon chain,
$X_1$ and $X_2$ are each independently a halogen or a methoxy group, and
A is a group

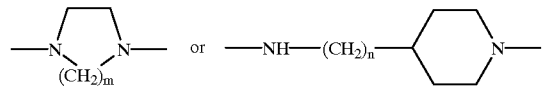

in which n is 0, 1, 2 or 3, and m is 2 or 3,
with a compound of formula VIII:

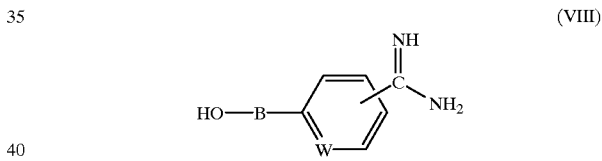

(VIII)

in which B is —CO—, —CO—$CH_2$, —CO—$CH_2$—O— or —CO—CH=CH—,
under conditions analogous to those of step (1°) of variant A above, to give a compound of the formula

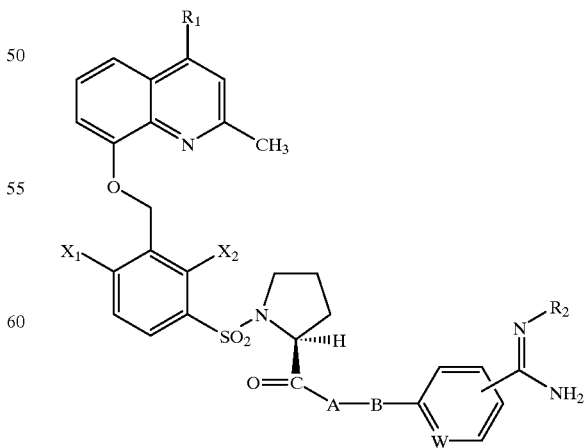

(I)

in which $R_1$, $X_1$ and $X_2$ are as defined above,

A is a group

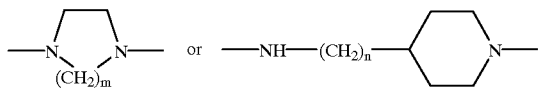

B is a group —CO—, —CO—CH$_2$—, —CO—CH$_2$—O— or —CO—CH=CH—, m is 2 or 3, n is 0, 1, 2 or 3, W is CH, and R$_2$ is a hydrogen atom; and (2°) if necessary, reacting the resulting compound of formula I with an acid to give the corresponding acid addition salt; or according to a third variant C, the steps which consist in:

(1°) reacting a compound of the formula

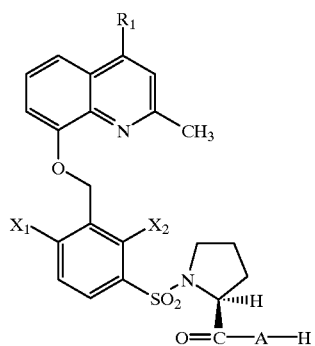

(VII)

in which:

R$_1$ is a hydrogen atom, a trifluoromethyl group or a C$_1$–C$_3$-alkyl group with a linear or branched hydrocarbon chain, X$_1$ and X$_2$ are each independently a halogen or a methoxy group, and A is a group

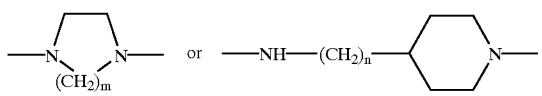

in which m is 2 or 3, and n is 0, 1, 2 or 3, with a compound of the formula

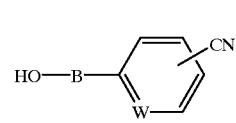

(IX)

in which B is —CO—, —CO—CH$_2$, —CO—CH$_2$—O— or —CO—CH=CH—, and W is CH or N, under conditions analogous to those described above for carrying out step 1 of variant A, to give a compound of the formula

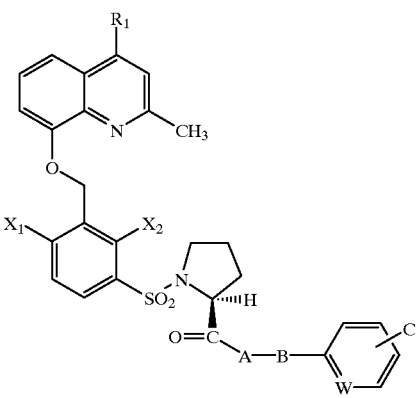

(X)

in which R$_1$, X$_1$, X$_2$, A, B and W are as defined in the starting compounds; (2°) reacting the resulting compound of formula X with hydroxylamine, in a solvent, for example DMSO, at room temperature, for 1 to 12 hours, to give the compound of the formula

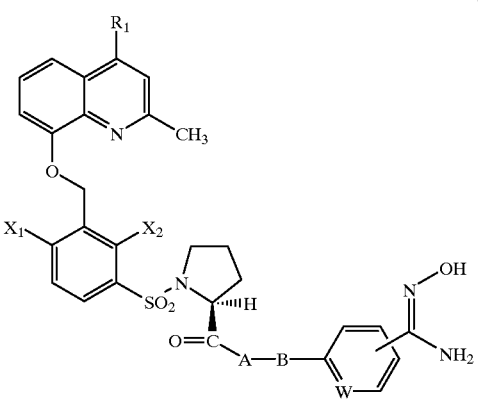

(XI)

in which R$_1$, X$_1$, X$_2$, A, B and W are as defined in the starting compounds;

(3°) reacting the resulting compound of formula XI with acetic anhydride, preferably in a solvent, for example dichloromethane, at room temperature, for 1 to 8 hours, to give the compound of the formula

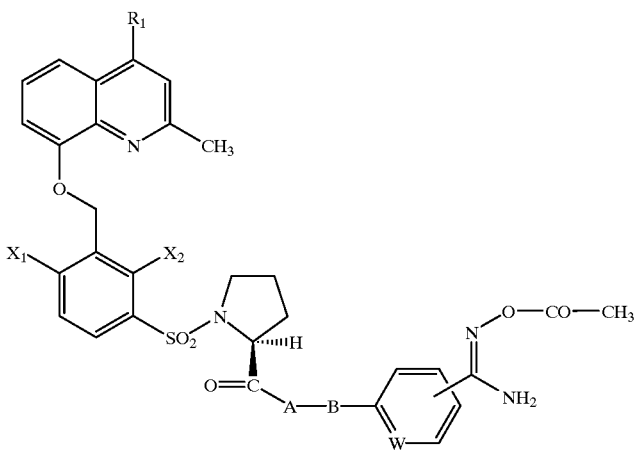

(XII)

in which $R_1$, $X_1$, $X_2$, A, B and W are as defined in the starting compounds;

(4°) reducing the resulting compound of formula XII by catalytic hydrogenation in the presence of a catalyst, for example Lindlar's catalyst, in a solvent, for example methanol, under a hydrogen pressure of about $10^5$ to $10^6$ pascals, at room temperature, to give the compound of the formula

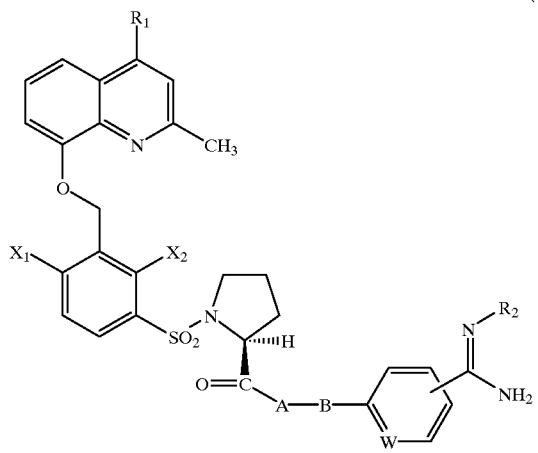

(I)

in which $R_1$, $X_1$, $X_2$, A, B and W are as defined in the starting compounds and $R_2$ is a hydrogen atom; and (5°) if necessary, obtaining the addition salt of the resulting compound of formula I by reaction with an appropriate acid.

The invention will be understood more clearly from the following Preparatory Examples and the results of pharmacological tests obtained with compounds according to the invention. In the case of compounds which have an asymmetric carbon in their structure, the absence of a particular indication, or the notation (R,S), means that the compounds are racemic; in the case of compounds which exhibit chirality, this is indicated immediately after the numbering of the substituent carried by said asymmetric carbon; the symbol (R) or (S) is then used in accordance with the Cahn-Ingold-Prelog rules. The nomenclature used in the Examples is that recommended by Chemical Abstracts; thus, after reaction of the acid group with an amine, certain L-proline derivatives may become 2(S)-pyrrolidinecarboxamide derivatives.

In the experimental section, the "Preparations" relate to the intermediates and the "Examples" relate the products according to the invention.

The melting points (m.p.) indicated below are generally measured using a Koffler bench and are not corrected, so they represent instantaneous melting points.

The spectral characteristics of the nuclear magnetic resonance (NMR) signals are given for the proton ($^1H$) or for the 13 isotope of carbon ($^{13}C$); the chemical shift is indicated relative to the tetramethylsilane signal and is followed, in brackets, by the shape of the signal (s for singlet, d for doublet, t for triplet, q for quadruplet, m for multiplet, bs for broad signal) and the number of protons corresponding to the signal. By way of indication, the $^1H$ NMR spectra were run at 300 MHz.

PREPARATION I

1-[[3-[(2,4-Dimethylquinolin-8-yl)oxymethyl]-2,4-dichlorophenyl]sulfonyl]-N-[(3-cyanophenyl)methyl]-2(S)-pyrrolidinecarboxamide A solution of 4 g ($7.85.10^{-3}$ mol) of N-[[3-[(2,4-dimethylquinolin-8-yl)oxymethyl]-2,4-dichlorophenyl]sulfonyl]-L-proline in 40 ml of dichloromethane is prepared and 1.5 g ($7.85.10^{-3}$ mol) of 1-(3-dimethylaminopropyl)-3-ethylcarbodiimide hydrochloride (EDCI), 1.07 g ($7.85.10^{-3}$ mol) of 1-hydroxy-7-azabenzotriazole (HOAT) and then 1.14 g ($8.63.10^{-3}$ mol) of 3-(aminomethyl)benzonitrile are added. The reaction mixture is stirred at room temperature (15–25° C.) for 2 hours. 10 ml of 1 N sodium hydroxide solution are then added, after which the organic phase is decanted. The aqueous phase is extracted with dichloromethane and the combined organic phases are subsequently washed with water until the washings are neutral, dried over sodium sulfate and then concentrated under reduced pressure. The crude product is purified by chromatography on silica gel using a dichloromethane/methanol mixture (98/2; v/v) as the eluent to give 2.6 g of the expected product in the form of a white solid (yield=55%).

M.p.=94–98° C.

$[\alpha]_D^{23}$=−51° (c=0.32; CHCl$_3$)

PREPARATION II

1-[[3-[(2,4-Dimethylquinolin-8-yl)oxymethyl]-2,4-dichlorophenyl]sulfonyl]-N-[3-(aminothioxomethyl)phenylmethyl]-2(S)-pyrrolidinecarboxamide A solution of 2.1 g ($3.36.10^{-3}$ mol) of the compound obtained according to Preparation I in 30 ml of pyridine and 3 ml of triethylamine is prepared, hydrogen sulfide is bubbled into this solution for 0.5 h at room temperature and the mixture is then allowed to react for 24 hours at room temperature. Water is subsequently added and the mixture is then extracted with dichloromethane. The organic phase is washed with water, dried over sodium sulfate and concentrated under reduced pressure. The crude product obtained is purified by chromatography on silica gel using a dichloromethane/ethyl acetate mixture (1/1; v/v) as the eluent to give 0.8 g of the expected product in the form of a yellow solid (yield=35%).

M.p.=116–118° C.
$[\alpha]_D^{28}$=–51° (c=0.3; $CHCl_3$)

PREPARATION III

1-[[3-[(2,4-Dimethylquinolin-8-yl)oxymethyl]-2,4-dichlorophenyl]sulfonyl]-N-[3-[(imino)(methylthio)methyl]phenylmethyl]-2(S)-pyrrolidinecarboxamide hydroiodide A solution of 0.6 g ($0.9.10^{-3}$ mol) of the compound obtained according to Preparation II in 20 ml of acetone is prepared and 1.94 g ($13.6.10^{-3}$ mol) of methyl iodide are added. The reaction mixture is refluxed gently for 2 hours and then concentrated under reduced pressure to give 0.72 g of the expected product in the form of a yellow solid (yield=100%).

M.p.=146–148° C.
$[\alpha]_D^{28}$=–10° (c=0.3; $CH_3OH$)

EXAMPLE 1

1-[[3-[(2,4-Dimethylquinolin-8-yl)oxymethyl]-2,4-dichlorophenyl]sulfonyl]-N-[3-(aminoiminomethyl)phenylmethyl]-2(S)-pyrrolidinecarboxamide A solution of 0.72 g ($0.9.10^{-3}$ mol) of the compound obtained according to Preparation III and 0.21 g ($2.7.10^{-3}$ mol) of ammonium acetate in 20 ml of ethanol is refluxed for 2 hours. After removal of the solvent under reduced pressure, 10 ml of N aqueous sodium hydroxide solution are added and the mixture is extracted with dichloromethane. The combined organic phases are washed with water, dried over sodium sulfate and then concentrated under reduced pressure. The product obtained is purified by chromatography on $NH_2$-grafted silica gel (Lichroprep® $NH_2$ marketed by Merck) using a dichloromethane/methanol mixture (98/2; v/v) as the eluent to give 0.19 g of the expected product in the form of a white solid (yield=30%).

EXAMPLE 2

1-[[3-[(2,4-Dimethylquinolin-8-yl)oxymethyl]-2,4-dichlorophenyl]sulfonyl]-N-[3-(aminoiminomethyl)phenylmethyl]-2(S)-pyrrolidinecarboxamide dihydrochloride 0.19 g ($0.28.10^{-3}$ mol) of the compound obtained according to Example 1 is dissolved in 1 ml of 1 N hydrochloric acid and this solution is then lyophilized to give 0.2 g of the expected product in the form of a pale yellow solid.

M.p.=194–196° C.
$[\alpha]_D^{23}$=22° (c=0.34; $CH_3OH$)

PREPARATION IV

1-[[3-[(2,4-Dimethylquinolin-8-yl)oxymethyl]-2,4-dichlorophenyl]sulfonyl]-N-methyl-N-(4-cyanophenylmethyl)-2(S)-pyrrolidinecarboxamide The expected product is obtained in the form of a yellow solid (yield=80%) by following a procedure analogous to Preparation I, starting from 4-[(N-methyl)aminomethyl]benzonitrile.

M.p.=64° C.
$[\alpha]_D^{23}$=–39° (c=0.55; $CH_3OH$)

PREPARATION V

1-[[3-[(2,4-Dimethylquinolin-8-yl)oxymethyl]-2,4-dichlorophenyl]sulfonyl]-N-methyl-N-[4-(aminothioxomethyl)phenylmethyl]-2(S)-pyrrolidinecarboxamide The expected product is obtained (yield=60%) by following a procedure analogous to Preparation II, starting from the compound obtained according to Preparation IV.

M.p.=50° C.
$[\alpha]_D^{23}$=–44° (c=0.36; $CH_3OH$)

PREPARATION VI

1-[[3-[(2,4-Dimethylquinolin-8-yl)oxymethyl]-2,4-dichlorophenyl]sulfonyl]-N-methyl-N-[4-[(imino)(methylthio)methyl]phenylmethyl]-2(S)-pyrrolidinecarboxamide The expected product is obtained (yield=97%) by following a procedure analogous to Preparation III, starting from the compound obtained according to Preparation V.

M.p.=53° C.
$[\alpha]_D^{23}$=–7° (c=0.34; $CH_3OH$)

EXAMPLE 3

1-[[3-[(2,4-Dimethylquinolin-8-yl)oxymethyl]-2,4-dichlorophenyl]sulfonyl]-N-methyl-N-[4-(aminoiminomethyl)phenylmethyl]-2(S)-pyrrolidinecarboxamide The expected product is obtained in the form of a white solid (yield=50%) by following a procedure analogous to Example 1, starting from the compound obtained according to Preparation VI.

M.p.=100° C.
$[\alpha]_D^{23}$=–42° (c=0.31; $CH_3OH$)

EXAMPLE 4

1-[[3-[(2,4-Dimethylquinolin-8-yl)oxymethyl]-2,4-dichlorophenyl]sulfonyl]-N-methyl-N-[4-(aminoiminomethyl)phenylmethyl]-2(S)-pyrrolidinecarboxamide dihydrochloride The expected product is obtained in the form of a pale yellow solid (yield=70%) by following a procedure analogous to Example 2, starting from the compound obtained according to Example 3.

M.p.=205° C.
$[\alpha]_D^{23}$=16° (c=0.30; $CH_3OH$)

PREPARATION VII

1-[[3-[(2,4-Dimethylquinolin-8-yl)oxymethyl]-2,4-dichlorophenyl]sulfonyl]-N-(4-cyanophenylmethyl)-2(S)-pyrrolidinecarboxamide The expected product is obtained (yield=65%) by following a procedure analogous to Preparation I, starting from 4-(aminomethyl)benzonitrile.

M.p.=96–98° C.
$[\alpha]_D^{29}$=–56° (c=0.32; $CHCl_3$)

PREPARATION VIII

1-[[3-[(2,4-Dimethylquinolin-8-yl)oxymethyl]-2,4-dichlorophenyl]sulfonyl-N-[4-(aminothioxomethyl)phenylmethyl]-2(S)-pyrrolidinecarboxamide The expected product is obtained (yield=35%) by following a procedure analogous to Preparation II, starting from the compound obtained according to Preparation VII.

M.p.=106–110° C.

$[\alpha]_D^{29}$=+21° (c=0.28; CHCl$_3$)

PREPARATION IX

1-[[3-[(2,4-Dimethylquinolin-8-yl)oxymethyl]-2,4-dichlorophenyl]sulfonyl]-N-[4-[(imino)(methylthio)methyl]phenylmethyl]-2(S)-pyrrolidinecarboxamide The expected product is obtained (yield=95%) by following a procedure analogous to Preparation III, starting from the compound obtained according to Preparation VIII.

M.p.=150–152° C.

$[\alpha]_D^{23}$=−10° (c=0.30; CH$_3$OH)

EXAMPLE 5

1-[[3-[(2,4-Dimethylquinolin-8-yl)oxymethyl]-2,4-dichlorophenyl]sulfonyl]-N-[4-(aminoiminomethyl)phenylmethyl]-2(S)-pyrrolidinecarboxamide The expected product is obtained in the form of a white solid (yield=57%) by following a procedure analogous to Example 1, starting from the compound obtained according to Preparation IX.

M.p.=115–118° C.

$[\alpha]_D^{25}$=−42° (c=0.29; CH$_3$OH)

EXAMPLE 6

1-[[3-[(2,4-Dimethylquinolin-8-yl)oxymethyl]-2,4-dichlorophenyl]sulfonyl]-N-[4-(aminoiminomethyl)phenylmethyl]-2(S)-pyrrolidinecarboxamide bis (methanesulfonate)

A solution of 160 mg (0.25.10$^{-3}$ mol) of the compound obtained according to Example 5 in 5 ml of ethanol is prepared and a solution of 50.4 mg (0.525.10$^{-3}$ mol) of methanesulfonic acid in 2 ml of ethanol is then added. The reaction medium is stirred for 0.5 h at room temperature and then poured slowly into 50 ml of ethyl ether. The precipitate which forms is filtered off after about 0.5 h. The solid is washed with ether and then redissolved in 20 ml of distilled water. The solution obtained is lyophilized to give 210 mg of the expected product in the form of a white solid (yield=86%).

M.p.=180° C.

$[\alpha]_D^{25}$=−25° (c=0.32; CH$_3$OH)

PREPARATION X

1-[[3-(2-Methylquinolin-8-yl)oxymethyl]-2,4-dichlorophenyl]sulfonyl]-N-(4-cyanophenylmethyl)-2(S)-pyrrolidinecarboxamide The expected product is obtained (yield=76%) by following a procedure analogous to Preparation VII, starting from N-[[3-[(2-methylquinolin-8-yl)oxymethyl]-2,4-dichlorophenyl]sulfonyl]-L-proline.

M.p.=86–90° C.

$[\alpha]_D^{31}$=−46° (c=0.3 1; CH$_3$OH)

PREPARATION XI

1-[[3-[(2-Methylquinolin-8-yl)oxymethyl]-2,4-dichlorophenyl]sulfonyl]-N-14-(aminothioxomethyl)phenylmethyl]-2(S)-pyrrolidinecarboxamide The expected product is obtained (yield=47%) by following a procedure analogous to Preparation II, starting from the compound obtained according to Preparation X.

M.p.=130–132° C.

$[\alpha]_D^{31}$=+24° (c=0.30; CHCl$_3$)

PREPARATION XII

1-[[3-[(2-Methylquinolin-8-yl)oxymethyl]-2,4-dichlorophenyl]sulfonyl]-N-[4-[(imino)(methylthio)methyl]phenylmethyl]-2(S)-pyrrolidinecarboxamide The expected product is obtained (yield=99%) by following a procedure analogous to Preparation III, starting from the compound obtained according to Preparation XI.

M.p.=160–162° C.

$[\alpha]_D^{31}$=−20° (c=0.30; CH$_3$OH)

EXAMPLE 7

1-[[3-[(2-Methylquinolin-8-yl)oxymethyl]-2,4-dichlorophenyl]sulfonyl]-N-[4-(aminoiminomethyl)phenylmethyl]-2(S)-pyrrolidinecarboxamide The expected product is obtained in the form of a white solid (yield=35%) by following a procedure analogous to Example 1, starting from the compound obtained according to Preparation XII.

EXAMPLE 8

1-[[3-[(2-Methylquinolin-8-yl)oxymethyl]-2,4-dichlorophenyl]sulfonyl]-N-[4-(aminoiminomethyl)phenylmethyl]-2(S)-pyrrolidinecarboxamide dihydrochloride The expected product is obtained in the form of a pale yellow solid (yield 98%) by following a procedure analogous to Example 2, starting from the compound obtained according to Example 7.

M.p.=178–180° C.

$[\alpha]_D^{22}$=−35° (c=0.35; CH$_3$OH)

PREPARATION XIII

1-[[3-[(2-Methylquinolin-8-yl)oxymethyl]-2,4-dichlorophenyl]sulfonyl]-N-(3-cyanophenyl)-2(S)-pyrrolidinecarboxamide The expected product is obtained (yield=75%) by following a procedure analogous to Preparation X, starting from 3-aminobenzonitrile.

M.p.=112–114° C.

$[\alpha]_D^{21}$=−53° (c=0.33; CH$_3$OH)

PREPARATION XIV

1-[[3-[(2-Methylquinolin-8-yl)oxymethyl]-2,4-dichlorophenyl]sulfonyl]-N-[3-(aminothioxomethyl)phenyl]-2(S)-pyrrolidinecarboxamide The expected product is obtained (yield=50%) by following a procedure analogous to Preparation II, starting from the compound obtained according to Preparation XIII.

M.p.=134–136° C.

$[\alpha]_D^{22}$=−130° (c=0.32; CHCl$_3$)

PREPARATION XV

1-[[3-[(2-Methylquinolin-8-yl)oxymethyl]-2,4-dichlorophenyl]sulfonyl]-N-[3-[(imino)(methylthio)methyl]phenyl]-2(S)-pyrrolidinecarboxamide The expected product is obtained (yield=95%) by following a procedure analogous to Preparation III, starting from the compound obtained according to Preparation XIV.

M.p.=160–164° C.

$[\alpha]_D^{22}$=−42° (c=0.32; CH$_3$OH)

EXAMPLE 9

1-[[3-[(2-Methylquinolin-8-yl)oxymethyl]-2,4-dichlorophenyl]sulfonyl-N-[3-(aminoiminomethyl)phenyl]-2(S)-pyrrolidinecarboxamide The expected product is obtained in the form of a white solid (yield=11%) by following a procedure analogous to Example 1, starting from the compound obtained according to Preparation XV.

$^1$H NMR (DMSO) 1.90–2.02 (m, 3H); 2.27 (m, 1H); 2.60 (s, 3H); 3.37–3.40 (m, 1H); 3.58 (m, 4.57–4.59 (m, 1H); 5.52 (m, 2H); 6.47 (broad m, 3H); 7.29–7.56 (m, 7H); 7.65–7.67 (d, 1H); 7.76–7.78 (d, 1H); 7.90 (m, 1H); 8.10–8.13 (d, 1H); 8.20–8.23 (d, 1H).

EXAMPLE 10

1-[[3-[(2-Methylquinolin-8-yl)oxymethyl]-2,4-dichlorophenyl]sulfonyl]-N-[3-(aminoiminomethyl)phenyl]-2(S)-pyrrolidinecarboxamide dihydrochloride The expected product is obtained in the form of a pale yellow solid (yield 99%) by following a procedure analogous to Example 2, starting from the compound obtained according to Example 9.

M.p.=192–195° C.

$[\alpha]_D^{22}$−37° (c=0.31; CH$_3$OH)

PREPARATION XVI

1-[[3-[(2,4-Dimethylquinolin-8-yl)oxymethyl]-2,4-dichlorophenyl]sulfonyl]-2(S)-[(piperazin-1-yl)carbonyl]pyrrolidine This compound is obtained from its addition salt with trifluoroacetic acid by reaction with aqueous sodium hydroxide solution, extraction with ethyl acetate and removal of the solvent under reduced pressure.

M.p.=169° C.

$[\alpha]_D^{25}$=−2.7° (c=0.44; CHCl$_3$)

EXAMPLE 11

1-[[3-[(2,4-Dimethylquinolin-8-yl)oxymethyl]-2,4-dichlorophenyl]sulfonyl]-2(S)-[[4-[4-(aminoiminomethyl)benzoyl]piperazin-1-yl]carbonyl]pyrrolidine A suspension of 0.261 g (1.3.10$^{-3}$ mol) of 4-(aminoiminomethyl)benzoic acid hydrochloride in 10 ml of dimethylformamide is prepared and 0.182 g (0.95.10$^{-3}$ mol) of EDCI and 0.13 g (0.95.103 mol) of HOBT are added. The mixture is stirred at room temperature for 15 minutes and 0.5 g (0.86.10$^{-3}$ mol) of the compound obtained according to Preparation XVI is then added. The reaction mixture is stirred for 4 hours at room temperature and then poured into iced water. 1 N sodium hydroxide solution is added slowly to bring the pH to 8, and the mixture is extracted several times with dichloromethane. The combined organic phases are washed with water, dried over sodium sulfate and concentrated under reduced pressure. The crude product is purified by chromatography on NH$_2$-grafted silica gel (Lichroprep® NH$_2$) using a dichloromethane/methanol mixture (95/5; v/v) as the eluent to give 0.4 g of the expected product in the form of a white solid (yield=64%).

M.p.=139° C.

$[\alpha]_D^{22}$=−31° (c=0.33; CH$_3$OH)

EXAMPLE 12

1-[[3-[(2,4-Dimethylquinolin-8-yl)oxymethyl]-2,4-dichlorophenyl]sulfonyl]-2(S)-[[4-[4-(aminoiminomethyl)benzoyl]piperazin-1-yl]carbonyl]pyrrolidine dihydrochloride A solution of 0.35 g (0.48.10$^{-3}$ mol) of the compound obtained according to Example 11 in 8 ml of ethyl acetate and 2 ml of ethanol is prepared. 0.5 ml of a saturated solution of hydrogen chloride in ethyl ether is added. The crystals formed are filtered off, washed with ethyl ether and then redissolved in 20 ml of distilled water. Lyophilization of the solution gives 0.35 g of the expected product in the form of a pale yellow solid (yield=90%).

M.p.=211° C.

$[\alpha]_D^{22}$=−11° (c=0.34; CH$_3$OH)

EXAMPLE 13

1-[[3-[(2,4-Dimethylquinolin-8-yl)oxymethyl]-2,4-dichlorophenyl]sulfonyl]-2(S)-[[4-[2-14-(aminoiminomethyl)phenyl]-1-oxo ethyl]piperazin-1-yl]carbonyl]pyrrolidine The expected product is obtained in the form of a beige solid (yield=74%) by following a procedure analogous to Example 11, starting from 4-(aminoiminomethyl)phenylacetic acid hydrochloride.

M.p.=126° C.

$[\alpha]_D^{27}$=−32° (c=0.32; CH$_3$OH)

EXAMPLE 14

1-[[3-[(2,4-Dimethylquinolin-8-yl)oxymethyl]-2,4-dichlorophenyl]sulfonyl]-(S)-[[4-[2-[4-(aminoiminomethyl)phenyl]-1-oxoethyl]piperazin-1-yl]carbonyl]pyrrolidine dihydrochloride The expected product is obtained in the form of an amorphous white solid yield=88%) by following a procedure analogous to Example 12, starting from the compound obtained according to Example 13.

M.p.=200° C.

$[\alpha]_D^{27}$=+20° (c=0.35; CH$_3$OH)

EXAMPLE 15

1-[[3-[(2,4-Dimethylquinolin-8-yl)oxymethyl]-2,4-dichlorophenyl]sulfonyl]-2(S)-[[4-[2-[4-(aminoiminomethyl)phenoxy]-1-oxoethyl]piperazin-1-yl]carbonyl]pyrrolidine The expected product is obtained in the form of a beige solid (yield=77%) by following a procedure analogous to Example 11, starting from 4-(aminoiminomethyl)
phenoxyacetic acid hydrochloride.

M.p.=128° C.

$[\alpha]_D^{27}$=−32° (c=0.35; CH$_3$OH)

EXAMPLE 16

1-[[3-[(2,4-Dimethylquinolin-8-yl)oxymethyl]-2,4-
dichlorophenyl]sulfonyl]-2(S)-[[4-[2-[4-
(aminoiminomethyl)phenoxyl]-1-oxoethyl]
piperazin-1-yl]carbonyl]pyrrolidine dihydrochloride The expected product is obtained in the form of a cream-colored solid (yield=95%) by following a procedure analogous to Example 12, starting from the compound obtained according to Example 15.

M.p.=213° C.

$[\alpha]_D^{27}$=+22° (c=0.37; CH$_3$OH)

EXAMPLE 17

1-[[3-[(2-Methylquinolin-8-yl)oxymethyl]-2,4-
dichlorophenyl]sulfonyl]-2(S)-[[4-[4-
(aminoiminomethyl)benzoyl]piperazin-1-yl]
carbonyl]pyrrolidine The expected product is obtained in the form of a white solid (yield=52%) by following a procedure analogous to Example 11, starting from 1-[[3-[(2-methylquinolin-8-yl)oxymethyl]-2,4-dichlorophenyl]sulfonyl]-2(S)-[(piperazin-1-yl)carbonyl]pyrrolidine.

M.p.=152° C.

$[\alpha]_D^{27}$=−37° (c=0.32; CH$_3$OH)

EXAMPLE 18

1-[[3-[(2-Methylquinolin-8-yl)oxymethyl]-2,4-
dichlorophenyl]sulfonyl]-2(S)-[[4-[4-
(aminoiminomethyl)benzoyl]piperazin-1-yl]
carbonyl]pyrrolidine dihydrochloride The expected product is obtained in the form of a creamy white solid (yield=95%) by following a procedure analogous to Example 12, starting from the compound obtained according to the preparation of Example 17.

M.p.=208° C.

$[\alpha]_D^{28}$=+10° (c=0.37; CH$_3$OH)

EXAMPLE 19

1-[[3-[(2-Methylquinolin-8-yl)oxymethyl]-2,4-
dichlorophenyl]sulfonyl]-2(S)-[[4-[2-[4-
(aminoiminomethyl)phenyl]-1-oxoethyl]piperazin-1-
yl]carbonyl]pyrrolidine The expected product is obtained in the form of a white solid (yield=86%) by following a procedure analogous to Example 17, starting from 4-(aminoiminomethyl)phenylacetic acid hydrochloride.

M.p.=155° C.

$[\alpha]_D^{28}$=+0.6° (c=0.35; DMSO)

EXAMPLE 20

1-[[3-[(2-Methylquinolin-8-yl)oxymethyl]-2,4-
dichlorophenyl]sulfonyl]-2(S)-[[4-[2-[4-
(aminoiminomethyl)phenyl-1-oxoethyl]piperazin-1-
yl]carbonyl]pyrrolidine dihydrochloride The expected product is obtained in the form of an amorphous cream-colored solid (yield=90%) by following a procedure analogous to Example 12, starting from the compound obtained according to Example 19.

M.p.=188° C.

$[\alpha]_D^{30}$=+12° (c=0.36; CH$_3$OH)

EXAMPLE 21

1-[[3-[(2-Methylquinolin-8-yl)oxymethyl]-2,4-
dichlorophenyl]sulfonyl]-2(S)-[[4-[2-[4-
(aminoiminomethyl)phenoxy-1-oxoethyl]piperazin-
1-yl]carbonyl]pyrrolidine The expected product is obtained in the form of a white solid (yield=60%) by following a procedure analogous to Example 17, starting from 4-(aminoiminomethyl)phenoxyacetic acid hydrochloride.

M.p.=130° C.

$[\alpha]_D^{30}$=−32.5° (c=0.36; DMSO)

EXAMPLE 22

1-[[3-[(2-Dimethylquinolin-8-yl)oxymethyl]-2,4-
dichlorophenyl]sulfonyl]-2(S)-[4-[2-[4-
(aminoiminomethyl)phenoxyl-1-oxoethyl]piperazin-
1-yl]carbonyl]pyrrolidine dihydrochloride The expected product is obtained in the form of a light beige solid (yield 86%) by following a procedure analogous to Example 12, starting from the compound obtained according to Example 21.

M.p.=215° C.

$[\alpha]_D^{28}$=+11° (c=0.4; CH$_3$OH)

EXAMPLE 23

1-[[3-[(2-Methylquinolin-8-yl)oxymethyl]-2,4-
dichlorophenyl]sulfonyl]-N-[1-[4-
(aminoiminomethyl)benzoyl]piperidin-4-yl]-2(S)-
pyrrolidinecarboxamide A solution of 0.48 g (2.39.10$^{-3}$ mol) of 4-(aminoiminomethyl)benzoic acid in 40 ml of dimethylformamide is prepared and 0.5 g (2.63.10$^{-3}$ mol) of EDCI and 0.36 g (2.63.10$^{-3}$ mol) of HOAT are added. After this mixture has been stirred for one hour at room temperature, 1.5 g (2.3.10$^{-3}$ mol) of 1-[[3-[(2-methylquinolin-8-yl)oxymethyl-2,4-dichlorophenyl]sulfonyl]-N-[piperidin-4-yl]-2(S)-pyrrolidinecarboxamide dihydrochloride and 0.5 g (5.5.10$^{-3}$ mol) of N-methylmorpholine are added and the reaction medium is stirred for 1 hour. It is then concentrated under reduced pressure, taken up with 200 ml of 3 N sodium hydroxide solution and extracted with dichloromethane. The organic phase is washed with water, dried over sodium sulfate and concentrated under reduced pressure. The crude product is purified by chromatography on NH$_2$-grafted silica gel (Lichroprep® NH$_2$) using a dichloromethane/ethanol mixture (95/5; v/v) as the eluent to give 0.33 g of the expected product in the form of white crystals (yield=19%).

$^1$H NMR (DMSO) 1.36 (m, 2H); 1.70 (m, 1H); 1.84 (m, 3H); 1.99 (m, 1H); 2.13 (m, 1H); 2.60 (s, 3H); 3.02 (m, 1H); 3.12 (m, 1H); 3.34 (m, 2H); 3.53 (m, 1H); 3.74 (m, 1H); 4.25 (m, 1H); 4.34 (m, 1H); 5.53 (s, 2H); 7.44 (m, 4H); 7.56 (d, 2H); 7.85 (m, 3H); 7.99 (d, 1H); 8.10 (d, 1H); 8.22 (d, 1H); 8.97 (broad s, 3H)

EXAMPLE 24

1-[[3-[(2-Methylquinolin-8-yl)oxymethyl]-2,4-
dichlorofonyl]sulfonyl]-N-1-[4-
(aminoiminomethyl)benzoyl]piperidin-4-yl]-2(S)-
pyrrolidinecarboxamide bis(methanesulfonate)

The expected product is obtained with in the form of a white powder (yield=66%) by following a procedure analogous to Example 6, starting from the compound obtained according to Example 23.

M.p.=184–188° C.

$[\alpha]_D^{25}$=−6.7° (c=0.67; CH$_3$OH)

PREPARATION XVII

1-[[3-[(2,4-Dimethylquinolin-8-yl)oxymethyl]-2,4-dichlorophenyl]sulfonyl-N-[piperidin-4-yl]-2(S)-pyrrolidinecarboxamide dihydrochloride This compound is obtained by a process analogous to the synthesis of 1-[[3-[(2-methylquinolin-8-yl)oxymethyl]-2,4-dichlorophenyl]sulfonyl]-N-[piperidin-4-yl]-2(S)-pyrrolidinecarboxamide hydrochloride described above, the 8-hydroxy-2-methylquinoline being replaced with 8-hydroxy-2,4-dimethylquinoline.

M.p.=184–186° C.

$[\alpha]_D^{25}$−14.2° (c=0.56; CH$_3$OH)

PREPARATION XVIII

1-[[3-[(2,4-Dimethylquinolin-8-yl)oxymethyl]-2,4-dichlorophenyl]sulfonyl]-N-[(piperidin-4-yl)methyl]-2(S)-pyrrolidinecarboxamide dihydrochloride This compound is obtained by following a procedure analogous to the process of Preparation XVII, but replacing the protected derivative of 4-aminopiperidine with a protected derivative of 4-(aminomethyl)piperidine.

M.p.=195° C.

$[\alpha]_D^{24}$=−32.2° (c=1; CH$_3$OH)

EXAMPLE 25

1-[[3-[(2,4-Dimethylquinolin-8-yl)oxymethyl]-2,4-dichlorophenyl]sulfonyl]-N-[1-[4-(aminoiminomethyl)benzoyl]piperidin-4-yl]-2(S)-pyrrolidinecarboxamide The expected product is obtained with (yield=36%) by following a procedure analogous to Example 23, starting from the compound obtained according to Preparation XVII.

$^1$H NMR (DMSO) 1.30 (m, 2H); 1.70 (m. 1H); 1.84 (m, 3H); 1.98 (m, 1H); 2.11 (m, 1H); 2.55 (s, 3H); 2.62 (s, 3H); 3.02 (m, 2H); 3.40 (m, 2H); 3.56 (m, 1H); 3.75 (m, 1H); 4.33 (m, 2H); 5.52 (s, 2H); 6.53 (broad m, 3H); 7.28 (s, 1H); 7.37 (d, 3H); 7.48 (t, 1H); 7.66 (d, 1H); 7.81 (m, 3H); 7.96 (d, 1H); 8.09 (d, 1H).

EXAMPLE 26

1-[[3-[(2,4-Dimethylquinolin-8-yl)oxymethyl]-2,4-dichlorophenyl]sulfonyl]-N-[1-[4-(aminoiminomethyl)benzoyl]piperidin-4-yl]-2(S)-pyrrolidinecarboxamide bis(methanesulfonate)

The expected product is obtained in the form of white crystals (yield=78%) by following a procedure analogous to Example 6.

M.p.=186–188° C.

$[\alpha]_D^{25}$=−9° (c=0.79; CH$_3$OH)

EXAMPLE 27

1-[[3-[(2,4-Dimethylquinolin-8-yl)oxymethyl]-2,4-dichlorophenyl]sulfonyl]-N-[1-[2-[4-(aminoiminomethyl)phenoxyl-1-oxoethyl]piperidin-4-yl]-2(S)-pyrrolidinecarboxamide The expected product is obtained (yield=47%) by following a procedure analogous to the process of Example 23, the product obtained according to Preparation XVII being reacted with 4-(aminoiminomethyl)phenoxyacetic acid.

$^1$H NMR (DMSO) 1.25 (m, 2H); 1.71 (m, 2H); 1.84 (m, 2H); 2.12 (m, 2H); 2.55 (s, 3H); 2.62 (s, 3H); 2.80 (m, 1H); 3.13 (m, 2H); 3.40 (m, 1H); 3.53 (m, 1H); 3.73 (m, 2H); 4.10 (m, 1H); 4.33 (m, 1H); 4.86 (m, 2H); 5.53 (s, 2H); 6.45 (broad m, 3H); 6.90 (d, 2H); 7.28 (s, 1H); 7.38 (d, 1H); 7.48 (t, 1H); 7.68 (t, 3H); 7.81 (d, 1H); 7.96 (d, 1H); 8.10 (d, 1H).

EXAMPLE 28

1-[[3-[(2,4-Dimethylquinolin-8-yl)oxymethyl]-2,4-dichlorophenyl]sulfonyl]-N-[1-[2-[4-(aminoiminomethyl)phenoxyl-1-oxoethyl]piperidin-4-yl]-2(S)-pyrrolidinecarboxamide bis (methanesulfonate)

The expected product is obtained in the form of white crystals (yield 72%) by following a procedure analogous to the process of Example 6.

M.p.=170° C.

$[\alpha]_D^{21}$=−4.2° (c=0.93; CH$_3$OH)

EXAMPLE 29

1-[[3-[(2,4-Dimethylquinolin-8-yl)oxymethyl]-2,4-dichlorophenyl]sulfonyl]-N-[[1-[2-[4-(aminoiminomethyl)phenoxy]-1-oxoethyl]piperidin-4-yl]methyl]2-(S)-pyrrolidinecarboxamide The expected product is obtained in the form of white crystals (yield=42%) by following a procedure analogous to Example 27, starting from the compound obtained according to Preparation XVIII.

$^1$H NMR (DMSO) 1.10 (m, 2H); 1.64 (m, 3H); 1.86 (m, 2H); 2.05 (m, 1H); 2.14 (m, 1H); 2.56 (s, 3H); 2.64 (s, 3H); 2.97 (m, 3H); 3.39 (m, 2H); 3.56 (m, 1H); 3.85 (m, 1H); 4.29 (m, 1H); 4.36 (m, 1H); 4.85 (s, 2H); 5.55 (s, 2H); 6.60 (broad m, 3H); 6.92 (d, 2H); 7.30 (s, 1H); 7.40 (d, 1H); 7.50 (t, 1H); 7.69 (t, 3H); 7.84 (d, 1H); 8.05 (m, 1H); 8.12 (d, 1H).

EXAMPLE 30

1-[[3-[(2,4-Dimethylquinolin-8-yl)oxymethyl]-2,4-dichlorophenyl]sulfonyl]-N-[[1-[2-[4-(aminoiminomethyl)phenoxy]-1-oxoethyl]piperidin-4-yl]methyl]-2(S)-pyrrolidinecarboxamide bis (methanesulfonate)

The expected product is obtained in the form of white crystals (yield=70%) by following a procedure analogous to Example 6, starting from the compound obtained according to Example 29.

M.p.=170° C.

$[\alpha]_D^{21}$=−19° (c=0.91; CH$_3$OH)

EXAMPLE 31

1-[[3-[2,4-Dimethylquinolin-8-yl)oxymethyl]-2,4-dichlorophenyl]sulfonyl]-N-[[1-[2-[4-(aminoiminomethyl)phenyl]-1-oxoethyl]piperidin-4-yl]methyl]-2(S)-pyrrolidinecarboxamide The expected product is obtained in the form of pale yellow crystals (yield=44%) by following a procedure analogous to Example 23, starting from the compound obtained according to Preparation XVIII and 4-(aminoiminomethyl)phenylacetic acid hydrochloride.

M.p.=130–132° C.

$[\alpha]_D^{20}$=−28° (c=0.90; CH$_3$OH)

EXAMPLE 32

1-[[3-[(2,4-Dimethylquinolin-8-yl)oxymethyl]-2,4-dichlorophenyl]sulfonyl]-N-[[1-[2-[4-(aminoiminomethyl)phenyl]-1-oxoethyl]piperidin-4-yl]methyl]-2(S)-pyrrolidinecarboxamide dihydrochloride The expected product is obtained in the form of white crystals (yield=77%) by following a procedure analogous to Example 12, starting from the compound obtained according to Example 31.

M.p.=210–214° C.

$[\alpha]_D^{24}$=–17.5° (c=0.75; $CH_3OH$)

EXAMPLE 33

1-[3-[(2,4-Dimethylquinolin-8-yl)oxymethyl]-2,4-dichlorophenyl]sulfonyl]-N-[1-[2-[4-(aminoiminomethyl)benzoyl]piperidin-4-yl]methyl]-2(S)-pyrrolidinecarboxamide The expected product is obtained in the form of an off-white solid (yield=59%) by following a procedure analogous to Example 31, starting from 4-(aminoiminomethyl) benzoic acid hydrochloride.

EXAMPLE 34

1-[[3-(2,4-Dimethylquinolin-8-yl)oxymethyl]-2,4-dichlorophenyl]sulfonyl]-N-[1-[2-[4-(aminoiminomethyl)benzoyl]piperidin-4-yl]methyl]-2(S)-pyrrolidinecarboxamide dihydrochloride The expected product is obtained in the form of white crystals (yield=77%) by following a procedure analogous to Example 12, starting from the compound obtained according to Example 33.

M.p.=186–190° C.

$[\alpha]_D^{25}$=–19° (c=1.05; $CH_3OH$)

EXAMPLE 35

1-[[3-[(2-Methylquinolin-8-yl)oxymethyl]-2,4-dichlorophenyl]sulfonyl]-N-[[1-[4-(aminoiminomethyl)benzoyl]piperidin-4-yl]methyl]-2(S)-pyrrolidinecarboxamide dihydrochloride By following a procedure analogous to Example 23, starting from 4-(aminoiminomethyl)benzoic acid hydrochloride and 1-[[3-[(2-methylquinolin-8-yl)oxymethyl]-2,4-dichlorophenyl]sulfonyl]-N-[(piperidin-4-yl)methyl]-2(S)-pyrrolidinecarboxamide dihydrochloride, the expected product is obtained in the form of a powdery white solid (yield=39%) after purification by means of reversed phase chromatography on RP18-grafted silica gel using a water/acetonitrile/hydrochloric acid mixture (63/32/1; v/v/v) as the eluent.

M.p.=210° C.

$[\alpha]_D^{26}$=–28° (c=0.98; $CH_3OH$)

EXAMPLE 36

1-[[3-[(2-Methylquinolin-8-yl)oxymethyl]-2,4-dichlorophenyl]sulfonyl]-N-[[1-[2-[4-(aminoiminomethyl)phenyl]-1-oxoethyl]piperidin-4-yl]methyl]-2(S)-pyrrolidinecarboxamide The expected product is obtained in the form of yellow crystals (yield=36%) by following a procedure analogous to Example 23, starting from 4-(aminoiminomethyl)benzoic acid hydrochloride and 1-[[3-[(2-methylquinolin-8-yl)oxymethyl]-2,4-dichlorophenyl]sulfonyl]-N-[(piperidin-4-yl)methyl]-2(S)-pyrrolidinecarboxamide hydrochloride.

M.p.=120–126° C.

$[\alpha]_D^{26}$=–33° (c=0.95; $CH_3OH$)

EXAMPLE 37

1-[[3-[(2-Methylquinolin-8-yl)oxymethyl]-2,4-dichlorophenyl]sulfonyl]-N-[[1-[2-[4-(aminoiminomethyl)phenyl]-1-oxoethyl]piperidin-4-yl]methyl]-2(S)-pyrrolidinecarboxamide dihydrochloride The expected product is obtained in the form of white crystals (yield=77%) by following a procedure analogous to Example 12, starting from the compound obtained according to Example 36.

M.p.=186–190° C.

$[\alpha]_D^{26}$=–19° (c=1.05; $CH_3OH$)

EXAMPLE 38

1-[[3-[(2-Methylquinolin-8-yl)oxymethyl]-2,4-dichlorophenyl]sulfonyl]-N-[[1-[2-[4-(aminoiminomethyl)phenoxy]-1-oxoethyl]piperidin-4-yl]methyl]-2(S)-pyrrolidinecarboxamide The expected product is obtained in the form of yellow crystals (yield=73%) by following a procedure analogous to Example 31, starting from 4-(aminoiminomethyl) phenoxyacetic acid hydrochloride.

M.p.=134–138° C.

$[\alpha]_D^{25}$=–29° (c=1.05; $C_2H_5OH$)

EXAMPLE 39

1-[[3-[(2-Methylquinolin-8-yl)oxymethyl]-2,4-dichlorophenyl]sulfonyl]-N-[[1-[2-[4-(aminoiminomethyl)phenoxy]-1-oxoethyl]piperidin-4-yl]methyl]-2(S)-pyrrolidinecarboxamide dihydrochloride The expected product is obtained in the form of light yellow crystals (yield=79%) by following a procedure analogous to Example 12, starting from the compound obtained in Example 38.

M.p.=197–200° C.

$[\alpha]_D^{24}$=–22° (c=0.95; $CH_3OH$)

EXAMPLE 40

1-[[3-[(2,4-Dimethylquinolin-8-yl)oxymethyl]-2,4-dichlorophenyl]sulfonyl]-N-[1-[2-[4-(aminoiminomethyl)phenyl]-1-oxoethyl]piperidin-4-yl]-2(S)-pyrrolidinecarboxamide The expected product is obtained in the form of pale yellow crystals (yield=50%) by following a procedure analogous to Example 31, starting from the compound obtained according to Preparation XVII.

EXAMPLE 41

1-[[3-[(2,4-Dimethylquinolin-8-yl)oxymethyl]-2,4-dichlorophenyl]sulfonyl]-N-[1-[2-[4-(aminoiminomethyl)phenyl]-1-oxoethyl]piperidin-4-yl]-2(S)-pyrrolidinecarboxamide dihydrochloride The expected product is obtained in the form of white crystals (yield=82%) by following a procedure analogous to Example 12, starting from the compound obtained according to Example 40.

M.p.=205° C.

$[\alpha]_D^{21}$=−7.7° (c=1.10; $CH_3OH$)

EXAMPLE 42

1-[[3-[(2-Methylquinolin-8-yl)oxymethyl]-2,4-dichlorophenyl]sulfonyl]-N-[1-[2-[4-(aminoiminomethyl)phenyl]-1-oxoethyl]piperidin-4-yl]-2(S)-pyrrolidinecarboxamide The expected product is obtained in the form of yellow crystals (yield=52%) by following a procedure analogous to Example 23, starting from 4-(aminoiminomethyl)phenylacetic acid hydrochloride.

M.p.=114–120° C.

$[\alpha]_D^{26}$=−29° (c=0.95; $CH_3OH$)

EXAMPLE 43

1-[[3-[(2-Methylquinolin-8-yl)oxymethyl]-2,4-dichlorophenyl]sulfonyl]-N-[1-[2-[4-(aminoiminomethyl)phenyl]-1-oxoethyl]piperidin-4-yl]-2(S)-pyrrolidinecarboxamide dihydrochloride The expected product is obtained in the form of white crystals (yield=77%) by following a procedure analogous to Example 12, starting from the compound obtained according to Example 42.

M.p.=189–191° C.

$[\alpha]_D^{26}$=−10° (c=0.95; $CH_3OH$)

EXAMPLE 44

1-[[3-(2-Methylquinolin-8-yl)oxymethyl]-2,4-dichlorophenyl]sulfonyl]-N-[1-[2-[4-(aminoiminomethyl)phenoxy]-1-oxoethyl]piperidin-4-yl]-2(S)-pyrrolidinecarboxamide The expected product is obtained in the form of yellow crystals (yield=59%) by following a procedure analogous to the process of Example 42, starting from 4-(aminoiminomethyl)phenoxyacetic acid hydrochloride.

M.p.=134–138° C.

$[\alpha]_D^{24}$=−27° (c=0.95; $CH_3OH$)

EXAMPLE 45

1-[[3-[(2-Methylquinolin-8-yl)oxymethyl]-2,4-dichlorophenyl]sulfonyl]-N-[1-[2-[4-(aminoiminomethyl)phenoxy]-1-oxoethyl]piperidin-4-yl]-2(S)-pyrrolidinecarboxamide dihydrochloride The expected product is obtained in the form of white crystals (yield=78%) by following a procedure analogous to Example 12, starting from the compound obtained according to Example 44.

M.p.=195–200° C.

$[\alpha]_D^{24}$=−9° (c=1.00; $CH_3OH$)

PREPARATION XIX

1-[[3-[(2,4-Dimethylquinolin-8-yl)oxymethyl]-2,4-dichlorophenyl]sulfonyl]-2(S)-[[4-(3-cyanobenzoyl)piperazin-1-yl]carbonyl]pyrrolidine The expected product is obtained in the form of a powdery white solid (yield=86%) by following a procedure analogous to Example 11, starting from 3-cyanobenzoic acid.

M.p.=131° C.

$[\alpha]_D^{23}$=−13° (c=0.45; $CHCl_3$)

EXAMPLE 46

1-[[3-[(2,4-Dimethylquinolin-8-yl)oxymethyl]-2,4-dichlorophenyl]sulfonyl]-2(S)-[[4-[3-[(amino)(hydroxyimino)methyl]benzoyl]piperazin-1-yl]carbonyl]pyrrolidine A solution of 1.02 g (1.44.10$^{-3}$ mol) of the compound obtained according to Preparation XIX in 16 ml of dimethyl sulfoxide is prepared and 0.16 g (2.3.10$^{-3}$ mol) of hydroxylamine hydrochloride and then 0.48 g (4.76.10$^{-3}$ mol) of triethylamine are added. After stirring for 4 hours at room temperature, the same amounts of hydroxylamine hydrochloride and triethylamine are added again and stirring is continued for 12 hours. The reaction mixture is then poured into 200 ml of water. The precipitate obtained is filtered off and then dried under vacuum to give 0.7 g of the expected product in the form of a fine white solid (yield=66%).

M.p.=160° C.

$[\alpha]_D^{23}$=−4° (c=0.50; $CHCl_3$)

PREPARATION XX

1-[[3-[(2,4-Dimethylquinolin-8-yl)oxymethyl]-2,4-dichlorophenyl]sulfonyl]-2(S)-[[4-[3-[(acetoxyimino)(amino)methyl]benzoyl]piperazin-1-yl]carbonyl]pyrrolidine 90 mg (0.88.10$^{-3}$ mol) of acetic anhydride are added to a solution of 0.62 g (0.84.10$^{-3}$ mol) of the compound obtained according to Example 46 in 6 ml of tetrahydrofuran and the reaction mixture is stirred at room temperature for 30 min. 50 ml of dichloromethane are added and this organic phase is washed with water until the washings are neutral. The organic phase is dried over magnesium sulfate and then concentrated under reduced pressure to give 0.65 g of the expected product in the form of a white solid.

M.p.=130° C.

$[\alpha]_D^{23}$=−8° (c=0.25; $CHCl_3$)

EXAMPLE 47

1-[[3-[(2,4-Dimethylquinolin-8-yl)oxymethyl]-2,4-dichlorophenyl]sulfonyl]-2(S)-[[4-[3-(aminoiminomethyl)benzoyl]piperazin-1-yl]carbonyl]pyrrolidine A solution of 0.6 g (0.76.10$^{-3}$ mol) of the compound obtained according to Preparation XX in 10 ml of methanol is prepared, 30 mg of Lindlar's catalyst (containing 5% of palladium) are added and this mixture is stirred under a hydrogen atmosphere, at atmospheric pressure and at room temperature for 6 hours. After removal of the catalyst by filtration, the solution is concentrated under reduced pressure. The crude product obtained is purified by chromatography on $NH_2$-grafted silica gel (Lichroprep® $NH_2$) using a dichloromethane/methanol mixture (97/3; v/v) as the eluent to give 0.47 g of the expected product in the form of a pale yellow solid (yield=85%).

M.p.=158° C.

$[\alpha]_D^{22}$=+10° (c=0.50; $CHCl_3$)

EXAMPLE 48

1-[[3-[(2,4-Dimethylquinolin-8-yl)oxymethyl]-2,4-dichlorophenyl]sulfonyl]-2(S)-[[4-13-(aminoiminomethyl)benzoyl]piperazin-1-yl]carbonyl]pyrrolidine dihydrochloride A solution of 380 mg (0.52.10$^{-3}$ mol) of the compound obtained according to Example 47 in 4 ml of dichloromethane is prepared and 1 ml of a saturated solution of hydrogen chloride in ethyl ether is added. After the mixture has been stirred for 30 min, the precipitate obtained is filtered off and washed with a small amount of ethyl ether. After drying, the product is redissolved in 6 ml of water and the solution is filtered and lyophilized to give 389 mg of the expected product in the form of a white solid.

M.p.=210° C.

$[\alpha]_D^{20}$=+22° (c=0.65; $CH_3OH$)

EXAMPLE 49

1-[[3-[(2,4-Dimethylquinolin-8-yl)oxymethyl]-2,4-dichlorophenyl]sulfonyl]-N-[3-[4-(aminoiminomethyl)phenyl]propyl]-2(S)-pyrrolidinecarboxamide A solution of 1 g ($1.96.10^{-3}$ mol) of 1-[[3-[(2,4-dimethylquinolin-8-yl)oxymethyl]-2,4-dichlorophenyl]sulfonyl]-L-proline in 10 ml of DMF is prepared and 0.41 g ($2.16.10^{-3}$ mol) of EDCI and 0.29 g ($2.16.10^{-3}$ mol) of HOAT are added. After stirring for 30 min at room temperature, a solution of 0.54 g ($2.16.10^{-3}$ mol) of 3-[4-(aminoiminomethyl)phenyl]propanamine dihydrochloride in 7 ml of DMF and 0.22 g ($2.16.10^{-3}$ mol of N-methylmorpholine are added to the reaction medium. After stirring for 14 hours at room temperature, the reaction mixture is poured into 150 ml of iced water and 10 ml of 1 N sodium hydroxide solution. The product which precipitates is filtered off and redissolved in dichloromethane. The solution is washed with water and then dried over magnesium sulfate and concentrated under reduced pressure. The crude product is purified by chromatography on $NH_2$-grafted silica gel using a dichloromethane/ethanol mixture (96/4; v/v) as the eluent to give 500 mg of the expected product in the form of a crystalline white solid (yield=39%).

M.p.=130–134° C.

$[\alpha]_D^{24}$=-42° (c=0.33; $CHCl_3$)

EXAMPLE 50

1-[[3-[(2,4-Dimethylquinolin-8-yl)oxymethyl]-2,4-dichlorophenyl]sulfonyl]-N-[3-[[4-(aminoiminomethyl)phenyl]propyl]-2(S)-pyrrolidinecarboxamide dihydrochloride A solution of 230 mg ($0.34.10^{-3}$ mol) of the compound obtained according to Example 49 in 5 ml of methanol is prepared and 0.5 ml of a 4 N solution of hydrogen chloride in ethyl ether is added. After stirring for 15 min, the reaction mixture is concentrated under reduced pressure, the residue is redissolved in water and this solution is lyophilized to give 250 mg of the expected product in the form of light yellow crystals (yield=98%).

M.p.=188–190° C.

$[\alpha]_D^{25}$=-37° (c=0.31; $CH_3OH$)

EXAMPLE 51

1-[[3-[(2,4-Dimethylquinolin-8-yl)oxymethyl]-2,4-dichlorophenyl]sulfonyl]-N-[2-[4-(aminoiminomethyl)phenyl]ethyl]-2(S)-pyrrolidinecarboxamide dihydrochloride The expected product is obtained in the form of white crystals (yield=30%) by following a procedure analogous to Examples 49 and 50, starting from 2-[4-(aminoiminomethyl)phenyl]ethanamine dihydrochloride.

M.p.=190–194° C.

$[\alpha]_D^{24}$=-22° (c=0.36; $CH_3OH$)

PREPARATION XXI

1-[[3-[(2,4-Dimethylquinolin-8-yl)oxymethyl]-2,4-dichlorophenyl]sulfonyl]-2(S)-[[4-(1,1-dimethylethoxycarbonyl)hexahydro-1,4-diazepin-1-yl]carbonyl]pyrrolidine The expected product is obtained in the form of a white solid (yield=79%) by following a procedure analogous to Preparation I, starting from 1-(1,1-dimethylethoxycarbonyl)hexahydro-1,4-diazepine (or N-Boc-homopiperazine).

M.p.=60° C.

$[\alpha]_D^{25}$=-17° (c=0.34; $CH_3OH$)

PREPARATION XXII

1-[[3-[(2,4-Dimethylquinolin-8-yl)oxymethyl]-2,4-dichlorophenyl]sulfonyl]-2(S)-[(hexahydro-1,4-diazepin-1-yl)carbonyl]pyrrolidine A solution of 2.05 g ($2.96.10^{-3}$ mol) of the compound obtained according to Preparation XXI in 20 ml of dichloromethane is prepared. It is cooled to 0° C. and 0.32 g ($2.96.10^{-3}$ mol) of anisole and 5 ml of trifluoroacetic acid are added. The reaction mixture is stirred for 1 hour at 0° C. and 1 hour at room temperature and then concentrated under reduced pressure. The residue is taken up with water, and 1 N sodium hydroxide solution is added in a sufficient amount to bring the medium to pH 12. This aqueous phase is extracted with ethyl acetate and the organic phase obtained is washed with water, dried over sodium sulfate and concentrated under reduced pressure to give 1.68 g of the expected product in the form of a white solid (yield=95%).

M.p.=65° C.

$[\alpha]_D^{25}$=-27° (c=0.34; $CH_3OH$)

EXAMPLE 52

1-[[3-[(2,4-Dimethylquinolin-8-yl)oxymethyl]-2,4-dichlorophenyl]sulfonyl]-2(S)-[[4-[4-(aminoiminomethyl)benzoyl hexahydro-1,4-diazepin-1-yl]-carbonyl]pyrrolidine The expected product is obtained in the form of an off-white solid (yield=32%) by following a procedure analogous to Example 11, starting from the compound obtained according to Preparation XXII.

M.p.=180° C.

$[\alpha]_D^{24}$=-35° (c=0.30; $CH_3OH$)

EXAMPLE 53

1-[[3-(2,4-Dimethylquinolin-8-yl)oxymethyl]-2,4-dichlorophenyl]sulfonyl]-2(S)-[[4-[[4-(aminoiminomethyl)benzoyl]hexahydro-1,4-diazepin-1-yl]carbonyl]pyrrolidine dihydrochloride The expected product is obtained in the form of a white solid (yield=78%) by following a procedure analogous to Example 12, starting from the compound obtained according to Example 51.

M.p.=200° C.

$[\alpha]_D^{26}$=-5.5° (c=0.31; $CH_3OH$)

PREPARATION XXIII

1-[[3-[(2,4-Dimethylquinolin-8-yl)oxymethyl]-2,4-dichlorophenyl]sulfonyl]2-(S)-[[4-[3-(4-cyanophenyl)-1-oxo-2(E)-propenyl]piperazin-1-yl]carbonyl]pyrrolidine The expected product is obtained in the form of white crystals (yield=79%) by following a procedure analogous to Example 11, starting from 4-cyanocinnamic acid (HOAT is used instead of HOBT in this synthesis).

M.p.=118° C.

[α]$_D^{26}$=−12° (c=0.50; CHCl$_3$)

EXAMPLE 54

1-[[3-[(2,4-Dimethylquinolin-8-yl)oxymethyl]-2,4-dichlorophenyl]sulfonyl]-2(S)-[[4-[3-[4-[(amino)(hydroxyimino)methyl]phenyl-1-oxo-2(E)-propenyl]piperazin-1-yl]carbonyl]pyrrolidine The expected product is obtained in the form of a white solid (yield=94%) by following a procedure analogous to Example 46, starting from the compound obtained according to Preparation XXIII.

M.p.=186° C.

[α]$_D^{25}$=+17.5° (c=0.39; CH$_3$OH)

PREPARATION XXIV

1-[[3-[(2,4-Dimethylquinolin-8-yl)oxymethyl]-2,4-dichlorophenyl]sulfonyl]-2(S)-[[4-[3-[4-[(acetoxyimino)(amino)methyl]phenyl]-1-oxo-2(E)-propenyl]piperazin-1-yl]carbonyl]pyrrolidine The expected product is obtained in the form of white crystals (yield=87%) by following a procedure analogous to Preparation XX, starting from the compound obtained according to Example 54.

M.p.=134° C.

[α]$_D^{25}$=−16° (c=0.32; CHCl$_3$)

EXAMPLE 55

1-[[3-[(2,4-Dimethylquinolin-8-yl)oxymethyl]-2,4-dichlorophenyl]sulfonyl]-2(S)-[[4-[3-[4-(aminoiminomethyl)phenyl]-1-oxo-2(E)-propenyl]piperazin-1-yl]carbonyl]pyrrolidine The expected product is obtained in the form of white crystals (yield=96%) by following a procedure analogous to Example 47, starting from the compound obtained according to Preparation XXIV.

M.p.=155° C.

[α]$_D^{25}$=−13° (c=0.50; CH$_3$OH)

PREPARATION XXV

3-Amino-6-chloro-2-methoxytoluene hydrochloride

A solution of 32.57 g (0.16 mol) of 6-chloro-2-methoxy-3-nitrotoluene in 230 ml of ethyl acetate and 25 ml of ethanol is prepared and 182.25 g (0.8 mol) of stannous chloride (dihydrate) are added slowly at room temperature, with stirring. The reaction medium is refluxed for 2 hours and then cooled and poured into water. 1 N sodium hydroxide solution is added to bring the pH to 13, and the mixture is extracted with dichloromethane. The organic phase is washed with water, dried over sodium sulfate and concentrated under reduced pressure. The gummy residue is dissolved in ethyl ether, and 167 ml of a 1 N solution of hydrogen chloride in ethyl ether are added. The salt which precipitates is filtered off, washed with ethyl ether and dried to give 24.5 g of the expected product in the form of violet crystals (yield=78%).

M.p.=162–168° C.

PREPARATION XXVI

4-Chloro-2-methoxy-3-methylbenzenesulfonyl chloride

A mixture of 10.46 g (0.05 mol) of the compound obtained according to Preparation XXV in 21 ml of concentrated hydrochloric acid and 6.5 ml of acetic acid is prepared. It is cooled to −10° C. and a solution of 3.76 g (0.054 mol) of sodium nitrite in 5.5 ml of water is added slowly. This diazonium salt solution is added slowly to a mixture, kept at 10° C., of 74 ml of acetic acid saturated with sulfur dioxide and 1.62 g of cuprous chloride. After stirring for 30 minutes at 10–15° C., the reaction mixture is poured into water and extracted twice with ethyl acetate. The combined organic phases are washed with sodium bicarbonate solution, with water and with saturated sodium chloride solution and then dried over sodium sulfate and concentrated under reduced pressure. The residue is purified by chromatography on silica gel using a cyclohexane/ethyl acetate mixture (95/5; v/v) as the eluent to give 3.6 g of the expected product in the form of yellow crystals (yield=62%).

M.p.=88–92° C.

PREPARATION XXVII

3-Bromomethyl-4-chloro-2-methoxybenzenesulfonyl chloride

A solution of 4.4 g (0.017 mol) of the compound obtained according to Preparation XXVI in 20 ml of 1,1,2,2-tetrachloroethane is prepared and 9.21 g (0.052 mol) of N-bromosuccinimide and 0.209 g (0.8.10$^{-3}$ mol) of benzoyl peroxide are added. The reaction mixture is heated at 135° C. for 3 hours, with stirring, and then cooled and poured into 250 ml of water. It is extracted with dichloromethane and the organic phase is washed with water, dried over sodium sulfate and concentrated under reduced pressure. The crude product obtained is purified by chromatography on silica gel using a cyclohexane/ethyl acetate mixture (95/5; v/v) as the eluent to give 3.6 g of the expected product in the form of yellow crystals (yield=62%).

M.p.=88–92° C.

PREPARATION XXVIII

1-[(3-Bromomethyl-4-chloro-2-methoxyphenyl)sulfonyl]-L-proline methyl ester

A solution of 1.7 g (0.01 mol) of L-proline methyl ester hydrochloride and 1.6 g of potassium bicarbonate in 5 ml of water is prepared and added slowly, with stirring, to a solution of 3.5 g (0.01 mol) of the compound obtained according to Preparation XXVII in 20 ml of acetonitrile. A further 1.6 g of potassium bicarbonate dissolved in 5 ml of water are then added. After stirring for 1 hour at room temperature, the reaction mixture is poured into water and extracted with ethyl acetate. The organic phase is washed with water, dried over sodium sulfate and concentrated under reduced pressure to give 4.13 g of the expected product in the form of an orange-yellow gum.

[α]$_D^{25}$=−33.5° (c=0.75; CHCl$_3$)

$^1$H NMR (CDCl$_3$) 1.8–2.1 (m, 4H); 3.35 (m, 1H); 3.56 (m, 1H); 3.68 (s, 3H); 4.12 (s, 3H); 4.6 (d, 1H); 4.68 (d, 1H); 7.31 (d, 1H); 7.85 (d, 1H).

PREPARATION XXIX

1-[[3-[(2,4-Dimethylquinolin-8-yl)oxymethyl]-4-chloro-2-methoxyphenyl]sulfonyl]-L-proline methyl ester A solution of 1.62 g (9.4.10$^{-3}$ mol) of 2,4-dimethyl-8-hydroxyquinoline in 10 ml of DMF is prepared and 0.281 g (9.4.10$^3$ mol) of sodium hydride (80% dispersion in oil) is added. After the mixture has been stirred for one hour at room temperature, a solution of 4 g (9.4.10⁻³ mol) of the compound obtained according to Preparation XXVIII in 30 ml of DMF is added dropwise. The reaction medium is stirred for 5 hours at room temperature and then poured into 400 ml of cold water. The precipitate formed is filtered off, washed with water on the filter and dried under vacuum to give 3.8 g of the expected product in the form of gray crystals (yield=78%).

M.p.=66–70° C.

$[\alpha]_D^{25}$=−8.5° (c=0.95; CHCl$_3$)

PREPARATION XXX

1-[[3-[(2,4-Dimethylquinolin-8-yl)oxymethyl]-4-chloro-2-methoxyphenyl]sulfonyl]-L-proline 8 ml of 1 N sodium hydroxide solution are added slowly to a solution of 3.76 g (7.2.10⁻³ mol) of the compound obtained according to Preparation XXIX in 35 ml of methanol and 35 ml of water. After stirring overnight at room temperature, the reaction mixture is poured into 200 ml of water and acidified with 1 N hydrochloric acid. The mixture is extracted with dichloromethane and the organic phase obtained is washed with water, dried over sodium sulfate and concentrated under reduced pressure. The crude product is purified by chromatography on silica gel using an ethyl acetate/ethanol mixture (9/1; v/v) as the eluent to give 1.73 g of the expected product in the form of beige crystals (yield=47%).

M.p.=134–138° C.

$[\alpha]_D^{26}$=+83° (c=0.98; CHCl$_3$)

PREPARATION XXXI

1-[[3-[(2,4-Dimethylquinolin-8-yl)oxymethyl]-4-chloro-2-methoxyphenyl]sulfonyl]-2(S)-[[4-(4-cyanobenzoyl)piperazin-1-yl]carbonyl]pyrrolidine The expected product is obtained in the form of white crystals (yield=96%) by following a procedure analogous to Example 49, starting from the acid compound obtained according to Preparation XXX and 1-(4-cyanobenzoyl)piperazine hydrochloride.

M.p.=139–141° C.

$[\alpha]_D^{26}$=−4.6° (c=0.98; CHCl$_3$)

EXAMPLE 56

1-[[3-[(2,4-Dimethylquinolin-8-yl)oxymethyl]-4-chloro-2-methoxyphenyl]sulfonyl]-2(S)-[[4-[4-[(amino)(hydroxyimino)methyl]benzoyl]piperazin-1-yl]carbonyl]pyrrolidine The expected product is obtained in the form of yellow crystals (yield=86%) by following a procedure analogous to Example 46, starting from the compound obtained according to Preparation XXXI.

M.p.=152–154° C.

$[\alpha_D^{26}$=−2.7° (c=1.00; DMSO)

PREPARATION XXXII

1-[[3-[(2,4-Dimethylquinolin-8-yl)oxymethyl]-4-chloro-2-methoxyphenyl]sulfonyl]-2(S)-[[4-[4-[(acetoxyimino)(amino)methyl]benzoyl]piperazin-1-yl]carbonyl]pyrrolidine The expected product is obtained in the form of white crystals (yield=98%) by following a procedure analogous to Preparation XX, starting from the compound obtained according to Example 56.

M.p.=110–112° C.

$[\alpha]_D^{26}$=−4.7° (c=1.00; CHCl$_3$)

EXAMPLE 57

1-[[3-[(2,4-Dimethylquinolin-8-yl)oxymethyl]-4-chloro-2-methoxyphenyl]sulfonyl]-2(S)-[[4-[4-(aminoiminomethyl)benzoyl]piperazin-1-yl]carbonyl]pyrrolidine The expected product is obtained in the form of yellow crystals (yield=71%) by following a procedure analogous to Example 47, starting from the compound obtained according to Preparation XXXII.

M.p.=147–150° C.

$[\alpha]_D^{26}$=−3.7° (c=0.75; CHCl$_3$)

EXAMPLE 58

1-[[3-[(2,4-Dimethylquinolin-8-yl)oxymethyl]-4-chloro-2-methoxyphenyl]sulfonyl]-2(S)-[[4-[4-(aminoiminomethyl)benzoyl]piperazin-1-yl]carbonyl]pyrrolidine dihydrochloride The expected product is obtained in the form of white crystals (yield=89%) by following a procedure analogous to Example 12, starting from the compound obtained according to Example 57.

M.p.=196–198° C.

$[\alpha]_D^{23}$=−21° (c=0.85; CH$_3$OH)

PREPARATION XXXII 4-(2-Methoxyphenylimino)-2-oxo-1,1,1-trifluoropentane

A mixture of 28.4 g (0.23 mol) of o-anisidine and 43.18 g (0.28 mol) of 1,1,1-trifluoro-2,4-pentanedione is heated at 100–105° C. for one hour and then cooled and the reaction medium is taken up with ethyl ether. 10 ml of 1 N hydrochloric acid are added. The mixture is filtered to remove the insoluble product, and the filtrate is concentrated under reduced pressure to give the expected product in the form of a beige solid (yield=98%).

M.p.=40–45° C.

PREPARATION XXXIII

8-Methoxy-2-methyl-4-trifluoromethylquinoline

A mixture of 400 g of polyphosphoric acid and 140 ml of toluene is prepared and a solution of 33.03 g (0.127 mol) of the compound obtained according to Preparation XXXII in 180 ml of toluene is added dropwise. The reaction mixture is refluxed gently for 17 hours, with stirring. It is cooled and iced water is added. The mixture is decanted and extracted several times with toluene. The combined organic phases are washed with water, dried over sodium sulfate and concentrated under reduced pressure to give 14.7 g of the expected product in the form of white crystals (yield=48%).

M.p.=112–113° C.

PREPARATION XXXIV

8-Hydroxy-2-methyl-4-trifluoromethylquinoline

A solution of 11 g (45.6.10⁻³ mol) of 8-methoxy-2-methyl-4-trifluoromethylquinoline in 360 ml of dichloromethane is cooled to −60° C. and 228 ml of a 1 M solution of boron tribromide in dichloromethane are added dropwise. The reaction medium is subsequently stirred for 1 hour at room temperature, 250 ml of methanol are then added slowly and stirring is continued for 2 hours. 250 ml of dichloromethane are added and sodium bicarbonate solution is added to render the medium alkaline. The organic phase is separated off, washed with water, dried over sodium sulfate and concentrated under reduced pressure to give 8.25 g of the expected product in the form of brown crystals (yield=79.5%).

M.p.=60–61° C.

PREPARATION XXXV

1-[[3-[(2-Methyl-3-trifluoromethylquinolin-8-yl) oxymethyl]-2,4-dichlorophenyl]sulfonyl]-L-proline methyl ester By following a procedure analogous to Preparation XXIX, starting from the compound obtained according to Preparation XXXIV, the expected product is obtained in the form of beige crystals (yield=88%) after purification by chromatography on silica gel.

M.p.=165–167° C.

PREPARATION XXXVI

1-[]3-[(2-Methyl-3-trifluoromethylquinolin-8-yl) oxymethyl-2,4-dichlorophenyl]sulfonyl]-L-proline The expected product is obtained (after concentration of the organic extraction phases) (yield=98%) by following a procedure analogous to Preparation XXX, starting from the compound obtained according to Preparation XXXV.

M.p.=120–125° C.

PREPARATION XXXVII

1-[[3-[(2-Methyl-4-trifluoromethylquinolin-8-yl) oxymethyl]-2,4dichlorophenyl]sulfonyl]-2(S)-[[4-(4-cyanobenzoyl)piperazin-1-yl]carbonyl]pyrrolidine The expected product is obtained (yield=55%) by following a procedure analogous to Preparation XXXI, starting from the compound obtained according to Preparation XXXVI.

M.p.=170–172° C.

EXAMPLE 59

1-[[3-1(2-Methyl-4-trifluoromethylquinolin-8-yl) oxymethyl]-2,4dichlorophenyl]sulfonyl]-2(S)-[[4-[4-[(amino)(hydroxyimino)methyl]benzoyl]piperazin-1-yl]carbonyl]pyrrolidine The expected product is obtained in the form of a creamy white powder (yield=79%) by following a procedure analogous to Example 46, starting from the compound obtained according to Preparation XXXVII.

M.p.=228–230° C.

$[\alpha]_D^{25}$=+2.5° (c=0.75; DMSO)

PREPARATION XXXVIII

1-[[3-[(2-Methyl-4-trifluoromethylquinolin-8-yl) oxymethyl]-2,4-dichlorophenyl]sulfonyl]-2(S)-[[4-[4-[(acetoxyimino)(amino)methyl]benzoyl] piperazin-1-yl]carbonyl]pyrrolidine The expected product is obtained in the form of white crystals (yield=97%) by following a procedure analogous to Preparation XX, starting from the compound obtained according to Example 59.

M.p.=244–246° C.

$[\alpha]_D^{25}$=+5° (c=1.05; DMSO)

EXAMPLE 60

1-[[3-[(2-Methyl-4-trifluoromethylquinolin-8-yl) oxymethyl]-2,4-dichlorophenyl]sulfonyl]-2(S)-[[4-[4-(aminoiminomethyl)benzoyl]piperazin-1yl] carbonyl]pyrrolidine The expected product is obtained in the form of a creamy white solid (yield=68%) by following a procedure analogous to Example 47, starting from the compound obtained according to Preparation XXXVIII.

M.p.=150–155° C. (dec.)

$[\alpha]_D^{25}$=−0.1° (c=0.85; CH$_2$Cl$_2$)

EXAMPLE 61

1-[[3-[(2-Methyl-4-trifluoromethylquinolin-8-yl) oxymethyl]-2,4-dichlorophenyl]sulfonyl]-2(S)-[[4-[4-(aminoiminomethyl)benzoyl] piperazin-1-yl] carbonyl]pyrrolidine bis(methanesulfonate)

The expected product is obtained in the form of a white solid (yield=92%) by following a procedure analogous to Example 6, starting from the compound obtained according to Example 60.

M.p.=132–135° C.

$[\alpha]_D^{22}$=+19° (c=1.00; Cl$_3$OH)

PREPARATION XXXIX

1-[[3-[(2,4-Dimethylquinolin-8-yl)oxymethyl]-2,4-dichlorophenyl]sulfonyl]2(S)-[[4-[(4-cyanophenyl) sulfonyl]piperazin-1-yl]carbonyl]pyrrolidine A suspension of 4 g (6.08.10$^{-3}$ mol) of the compound obtained according to Preparation XVII in 50 ml of dichloromethane is prepared, 2.46 g (24.3.10$^{-3}$ mol) of triethylamine are added and the mixture is cooled to 0° C. 1.47 g (7.3.10$^{-3}$ mol) of 4-cyanobenzenesulfonyl chloride are subsequently added dropwise, with stirring, and the reaction medium is then stirred for one hour at room temperature. 100 ml of dichloromethane are added and the reaction medium is poured into water. After decantation, the organic phase is washed with water, dried over sodium sulfate and concentrated under reduced pressure. The residue is purified by chromatography on silica gel using a dichloromethane/ ethanol mixture (95/5; v/v) as the eluent to give 2.9 g of the expected product in the form of a beige solid (yield=64%).

M.p.=156–158° C.

$[\alpha]_D^{24}$=−10.5° (c=0.6; CHCl$_3$)

EXAMPLE 62

1-[[3-[(2,4-Dimethylquinolin-8-yl)oxymethyl]-2,4-dichlorophenyl]sulfonyl]2(S)-[[4-[[4-[(amino) (hydroxyimino)methyl]phenyl]sulfonyl]piperazin-1-yl]carbonyl]pyrrolidine The expected product is obtained in the form of a white solid (yield=52%) by following a procedure analogous to Example 46 (the triethylamine is replaced with potassium t-butoxide), starting from the compound obtained according to Preparation XXXIX.

M.p.=154–156° C.

$[\alpha]_D^{26}=+46.5°$ (c=1.10; CHCl$_3$)

PREPARATION XL

1-[[3-[(2,4-Dimethylquinolin-8-yl)oxymethyl]-2,4-dichlorophenyl]sulfonyl]-2(S)-[[4-[[4-[(acetoxyimino)(amino)methyl]phenyl]sulfonyl]piperazin-1-yl]carbonyl]pyrrolidine The expected product is obtained in the form of beige crystals (yield=98%) by following a procedure analogous to Preparation XX, starting from the compound obtained according to Example 62.

M.p.=134–136° C.

$[\alpha9_D^{26}=+40°$ (c=0.85; CHCl$_3$)

EXAMPLE 63

1-[[3-[(2,4-Dimethylquinolin-8-yl)oxymethyl]-2,4-dichlorophenyl[sulfonyl]-2(S)-[[4-[[4-(aminoiminomethyl)phenyl]sulfonyl]piperazin-1-yl]carbonyl]pyrrolidine The expected product is obtained in the form of white crystals (yield=49%) by following a procedure analogous to Example 47, starting from the compound obtained according to Preparation XL.

M.p.=146–150° C.

$[\alpha]_D^{26}=+26°$ (c=0.85; CHCl$_3$)

EXAMPLE 64

1-[[3-[(2,4-Dimethylquinolin-8-yl)oxymethyl]-2,4-dichlorophenyl]sulfonyl]-2(S)-[[4-[[4-(aminoiminomethyl)phenyl]sulfonyl]piperazin-1-yl]carbonyl]pyrrolidine dihydrochloride The expected product is obtained in the form of a fine white solid (yield=90%) by following a procedure analogous to Example 12, starting from the compound obtained according to Example 63.

M.p.=152–155° C.

$[\alpha]_D^{27}=+28.5°$ (c=0.85; C$_2$H$_5$OH)

PREPARATION XLI

N-[[3-Cyanopyridin-2-yl]methyl]iminodicarboxylic acid bis(1,1-dimethylethyl)ester A solution of 3.8 g (17.5.10$^{-3}$ mol) of di-t-butyl iminodicarboxylate in 25 ml of THF is prepared and 0.525 g (17.5.10$^{-3}$ mol) of sodium hydride (as an 80% dispersion in oil) is added. After stirring for 15 min at room temperature, a solution of 3.45 g (17.5.10$^{-3}$ mol) of 6-bromomethyl-3-cyanopyridine in 50 ml of THF is added dropwise. After stirring for 30 minutes at room temperature, the mixture is concentrated under reduced pressure and the residue is purified by chromatography on silica gel using dichloromethane as the eluent to give 4 g of the expected product in the form of white crystals (yield=68.5%).

M.p.=65–70° C.

PREPARATION XLII

N-[[3-[(Amino)(hydroxyimino)methyl]pyridin-2-yl]methyl]iminodicarboxylic acid bis(1,1-dimethylethyl) ester The expected product is obtained in the form of white crystals (yield=54%) by following a procedure analogous to Example 62, starting from the compound obtained according to Preparation XLI.

M.p.=178–180° C.

PREPARATION XLIII

2-Aminomethyl-5-(aminoiminomethyl)pyridine trihydrochloride

A solution of 1.7 g (4.6.10$^{-3}$ mol) of the compound obtained according to Preparation XLII in 12 ml of acetic acid and 0.87 ml of acetic anhydride is prepared. 245 mg of 10% palladium-on-charcoal are added and the mixture is stirred under a hydrogen atmosphere, at atmospheric pressure and at room temperature for 2 hours. After the catalyst has been filtered off, 18.6 ml of 5 N hydrochloric acid are added and the mixture is stirred for 12 hours. 100 ml of 2-propanol and 200 ml of ethyl ether are then added. The precipitate formed is filtered off, washed with ethyl ether and dried under vacuum to give 720 mg of the expected product in the form of off-white crystals (yield=60%).

M.p.=275–280° C.

EXAMPLE 65

1-[[3-[(2,4-Dimethylquinolin-8-yl)oxymethyl]-2,4-dichlorophenyl]sulfonyl]-N-[[5-(aminoiminomethyl)pyridin-2-yl]methyl]-2(S)-pyrrolidinecarboxamide The expected product is obtained in the form of white crystals (yield=26%) by following a procedure analogous to Example 49, starting from the compound obtained according to Preparation XLIII.

M.p.=128–130° C.

$[\alpha]_D^{21}=-36°$ (c=1.00; CHCl$_3$)

EXAMPLE 66

1-[[3-[(2,4-Dimethylquinolin-8-yl)oxymethyl]-2,4-dichlorophenyl]sulfonyl]-N-[[5-(aminoiminomethyl)pyridin-2-yl]methyl]-2(S)-pyrrolidinecarboxamide dihydrochloride The expected product is obtained in the form of fine white crystals (yield=76%) by following a procedure analogous to Example 12, starting from the compound obtained according to Example 65.

M.p.=202–204° C. (dec.)

$[\alpha]_D^{23}=-49°$ (c=1.00; C$_2$H$_5$OH)

PREPARATION XLIV

1-[[3-[(2,4-Dimethylquinolin-8-yl)oxymethyl]-2,4-dichlorophenyl]sulfonyl]-2(S)-[[4-[(5-cyanopyridin-2-yl)carbonyl]piperazin-1-yl]carbonyl]pyrrolidine The expected product is obtained in the form of a pale yellow solid (yield=44%) by following a procedure analogous to Preparation XXIII, starting from 5-cyanopicolinic acid hydrochloride.

M.p.=125–128° C.

$[\alpha]_D^{21}=-12.5°$ (c=1.00; CHCl$_3$)

EXAMPLE 67

1-[[3-[(2,4-Dimethylquinolin-8-yl)oxymethyl]-2,4-dichlorophenyl]sulfonyl]-2(S)-[[4-[[5-[(amino)(hydroxyimino)methyl]pyridin-2-yl]carbonyl]piperazin-1-yl]carbonyl]pyrrolidine The expected product is obtained in the form of a beige solid (yield=45%) by following a procedure analogous to Example 62, starting from the compound obtained according to Preparation XLIV.

M.p.=148–150° C.

$[\alpha]_D^{25}$=+4.5° (c=1.05; CHCl$_3$)

PREPARATION XLV

1-[[3-[(2,4-Dimethylquinolin-8-yl)oxymethyl]-2,4-dichlorophenyl]sulfonyl]-2(S)-[[4-[[5-[(acetoxyimino)(amino)methyl]pyridin-2-yl]carbonyl]piperazin-1-yl]carbonyl]pyrrolidine The expected product is obtained in the form of a light yellow solid (yield=92%) by following a procedure analogous to Preparation XX, starting from the compound obtained according to Example 67.

M.p.=145–147° C.

$[\alpha]_D^{21}$=−4.4° (c=1.05; CHCl$_3$)

EXAMPLE 68

1-[[3-[(2,4-Dimethylquinolin-8-yl)oxymethyl]-2,4-dichlorophenyl]sulfonyl]-2(S)-[[4-[[5-(aminoiminomethyl)pyridin-2-yl]carbonyl]piperazin-1-yl]carbonyl]pyrrolidine The expected product is obtained in the form of a light yellow solid (yield=58%) by following a procedure analogous to Example 47, starting from the compound obtained according to Preparation XLV.

M.p.=150–155° C.

$[\alpha]_D^{20}$=−40.5° (c=0.95; CH$_3$OH)

EXAMPLE 69

1-[[3-[(2,4-Dimethylquinolin-]yl)oxymethyl]-2,4-dichlorophenyl]sulfonyl]-2(S)-[[4-[[S-(aminoiminomethyl)pyridin-2-yl]carbonyl]piperazin-1-yl]carbonyl]pyrrolidine methanesulfonate The expected product is obtained in the form of a pale yellow solid (yield=91%) by following a procedure analogous to Example 6, starting from the compound obtained according to Example 68.

M.p.=176–180° C.

$[\alpha]_D^{22}$=−32° (c=0.95; CH$_3$OH)

PREPARATION XLVI

1-[[3-[(2,4-Dimethylquinolin-8-yl)oxymethyl]-2,4-dichlorophenyl]sulfonyl]-2(S)-[[4-(4-cyanobenzoyl)piperazin-1-yl]carbonyl]pyrrolidine The expected product is obtained in the form of a colorless oil (yield=83%) by following a procedure analogous to Preparation XXIII, starting from 4-cyanobenzoic acid.

EXAMPLE 70

1-[[3-[(2,4-Dimethylquinolin-8-yl)oxymethyl]-2,4-dichlorophenyl]sulfonyl]-2(S)-[[4-[4-[(amino)(hydroxyimino)methyl]benzoyl]piperazin-1-yl]carbonyl]pyrrolidine The expected product is obtained in the form of white crystals (yield=34%) by following a procedure analogous to Example 62, starting from the compound obtained according to Preparation XLVI.

M.p.=161° C.

$[\alpha]_D^{24}$=−15° (c=0.55; CHCl$_3$)

PREPARATION XLVII 2,4-Dimethoxy-3-methylbenzenesulfonyl chloride

A solution of 15.22 g (0.1 mol) of 2,6-dimethoxytoluene in 50 ml of dichloromethane is prepared and 20 ml (0.3 mol) of chlorosulfonic acid are added at 0° C. The reaction medium is stirred for 1 hour at room temperature and then poured into 300 ml of iced water. The product is extracted with diisopropyl ether and the organic phases are washed with water, dried over magnesium sulfate and concentrated under reduced pressure to give 15.2 g of the expected product in the form of a crystalline light yellow solid (yield=61%).

M.p.=60° C.

PREPARATION XLVIII 2,4-Dimethoxy-3-(bromomethyl)benzenesulfonyl chloride

The expected product is obtained in the form of a light brown solid (yield=44%) by following a procedure analogous to Preparation XXVII, starting from the compound obtained according to Preparation XLVII.

M.p.=82° C.

PREPARATION IL

1-[(3-Bromomethyl-2,4-dimethoxyphenyl)sulfonyl]-L-proline methyl ester

The expected product is obtained in the form of a yellow oil (yield=69%) by following a procedure analogous to Preparation XXVIII, starting from the compound obtained according to Preparation XLVIII.

$^1$H NMR (CDCl$_3$) 1.74 –1.79 (m, 1H); 1.92–2.11 (m, 3H); 3.28–3.36 (m, 1H); 3.50–3.58 (m, 1H); 3.69 (s, 3H); 3.96 (s, 3H); 4.07 (s, 3H); 4.53–4.59 (m, 1H); 4.65–4.73 (dd, 2H); 6.74–6.77 (d, 1H); 7.91–7.94 (d, 1H).

PREPARATION L

1-[[3-[(2,4-Dimethylquinolin-8-yl)oxymethyl]-2,4-dimethoxyphenyl]sulfonyl]-L-proline methyl ester The expected product is obtained in the form of a white powder (yield=78%) by following a procedure analogous to Preparation XXIX, starting from the compound obtained according to Preparation IL.

M.p.=186° C.

PREPARATION LI

1-[[3-[(2,4-Dimethylquinolin-8-yl)oxymethyl]-2,4-dimethoxyphenyl]sulfonyl]-L-proline The expected product is obtained in the form of a creamy white solid (yield=97%) by following a procedure analogous to Preparation XXX, starting from the compound obtained according to Preparation L.

M.p.=130° C.

37

PREPARATION LII

1-[[3-[(2,4-Dimethylquinolin-8-yl)oxymethyl]-2,4-dimethoxyphenyl]sulfonyl]-2(S)-[[4-(4-cyanobenzoyl)piperazin-1-yl]carbonyl]pyrrolidine The expected product is obtained in the form of white crystals (yield=71%) by following a procedure analogous to Preparation XXXI, starting from the compound obtained according to Preparation LI.

M.p.=118–122° C.

EXAMPLE 71

1-[[3-[(2,4-Dimethylquinolin-8-yl)oxymethyl]-2,4-dimethoxyphenyl]sulfonyl]-2(S)-[[4-[4-[(amino)(hydroxyimino)methyl]benzoyl]piperazin-1-yl]carbonyl]pyrrolidine The expected product is obtained in the form of white crystals (yield=79%) by following a procedure analogous to Example 56, starting from the compound obtained according to Preparation LII.

M.p.=160–164° C.

PREPARATION LIII

1-[[3-[(2,4-Dimethylquinolin-8-yl)oxymethyl]-2,4-dimethoxyphenyl]sulfonyl]-2(S)-[[4-[4-[(acetoxyimino)(amino)methyl]benzoyl]piperazin-1-yl]carbonyl]pyrrolidine The expected product is obtained in the form of white crystals (yield=88%) by following a procedure analogous to Preparation XXXII, starting from the compound obtained according to Example 71.

M.p.=152° C.

EXAMPLE 72

1-[[3-[(2,4-Dimethylquinolin-8-yl)oxymethyl]-2,4-dimethoxyphenyl]sulfonyl]-2(S)-[[4-[4-(aminoiminomethyl)benzoyl]piperazin-1-yl]carbonyl]pyrrolidine The expected product is obtained in the form of beige crystals (yield=42%) by following a procedure analogous to Example 57, starting from the compound obtained according to Preparation LIII.

M.p.=136° C.

The activity of the products according to the invention was evaluated in respect of their ability to bind to the bradykinin receptors. Kinins, of which bradykinin is the main representative, actually form a group of small peptides which make an important contribution to the inflammatory response and therefore appear to be involved in the pathophysiology of inflammatory diseases. Furthermore, bradykinin is one of the most potent analgesics known. Kinins activate two types of receptor, called $B_1$ and $B_2$. The $B_2$ receptor belongs to the large family of receptors with seven transmembrane domains coupled to the G proteins. In the present invention we describe compounds which bind to the $B_2$ receptor and thereby block the binding of bradykinin.

The following pharmacological test is used: Ileum segments are isolated from male guinea-pigs [of the Dunkin-Hartley strain (Iffa Credo, l'Arbresle, France)] and ground in the following TES buffer: TES 25 mM, 1,10-phenanthroline 1 mM (pH 6.8), bacitracin 140 µg/ml, BSA 1 g/l. The membranes are then isolated by centrifugation (18,000 rpm; 20 min; 4° C.). The binding studies are carried out in this TES buffer using [$^3$H]-bradykinin (120 pM) and 50 µg of membrane protein per test (final volume 500 µl) with an equilibrium time of 90 min at 20° C. The percentage inhibition of the binding of [$^3$H]-bradykinin is then determined in the presence of one of the test compounds according to the invention at a concentration of $10^{-6}$ M.

The results obtained from these tests (shown as "activity") are collated in Table I below with reference to the Examples given in the description.

The compounds of the present invention which inhibit the binding of [$^3$H]-bradykinin to the guinea-pig $B_2$ receptor (see Table I) also bind to the human $B_2$ receptor cloned and transfected in a stable manner into CHO cells (Chinese Hamster Ovary cells). Thus, in this test, some compounds inhibit the binding of [$^3$H]-bradykinin to the $B_2$ receptor by at least 95% at a concentration of 10 µM.

The compounds of the present invention can be useful in the treatment of pain and particularly in the treatment of numerous pathological conditions involving bradykinin or its homologs. These pathological conditions include septic and hemorrhagic shock, anaphylactic reactions, arthrosis, rheumatoid polyarthritis, rhinitis, asthma, inflammatory diseases of the gastrointestinal tract (for example colitis, rectitis, Crohn's disease), pancreatitis, certain carcinomas, hereditary angioedema, migraine, encephalomyelitis, meningitis, cerebrovascular complications (especially those caused by cerebral traumatic shock), certain neurological disorders, vascular inflammatory states (for example atherosclerosis and arteritis of the lower limbs), painful states (for example headache, toothache, menstrual pain), premature uterine contractions, cystitis and burns. The compounds according to the invention can also be useful for the potentiation of antiviral agents.

The compounds of the present invention, which can be used in the form of the free base or in the form of their non-toxic addition salts in association with a physiologically acceptable excipient, are generally prescribed in human therapeutics at doses of about 1 to 1000 mg/day in a form which can be administered orally, by intravenous, intramuscular or subcutaneous injection, transdermally, by means of aerosols or by means of suppositories.

These compounds can also be administered topically, for example in the form of a gel or ointment.

The compounds of the present invention are also useful as pharmacological reagents, especially for the study of hormone-receptor interactions. Use as a pharmacological reagent may require a radiolabeled derivative of one of the compounds according to the invention (for example with tritium [$^3$H] or sulfur [$^{35}$S]) in order to obtain a radioligand intended for conformational studies of the bradykinin $B_2$ receptor or for binding tests involving this type of receptor, for example for the evaluation of novel compounds which are capable of exhibiting an affinity for the bradykinin $B_2$ receptor.

TABLE I

| Ex. | R₁ | X₂ | W | A | B | Pos. (a) | R₂ | Salt (b) | Activity (%) |
|---|---|---|---|---|---|---|---|---|---|
| 1 | CH₃ | Cl | CH | —NH—CH₂— | — | 3 | H | — | — |
| 2 | CH₃ | Cl | CH | —NH—CH₂— | — | 3 | H | Chl | 100 |
| 3 | CH₃ | Cl | CH | —N(CH₃)—CH₂— | — | 4 | H | — | — |
| 4 | CH₃ | Cl | CH | —N(CH₃)—CH₂— | — | 4 | H | Chl | 97.8 |
| 5 | CH₃ | Cl | CH | —NH—CH₂— | — | 4 | H | — | — |
| 6 | CH₃ | Cl | CH | —NH—CH₂— | — | 4 | H | Ms | 100 |
| 7 | H | Cl | CH | —NH—CH₂— | — | 4 | H | — | — |
| 8 | H | Cl | CH | —NH—CH₂— | — | 4 | H | Chl | 96.6 |
| 9 | H | Cl | CH | —NH— | — | 3 | H | — | — |
| 10 | H | Cl | CH | —NH— | — | 3 | H | Chl | 100 |
| 11 | CH₃ | Cl | CH | piperazine | —CO— | 4 | H | — | — |
| 12 | CH₃ | Cl | CH | piperazine | —CO— | 4 | H | Chl | 99.3 |
| 13 | CH₃ | Cl | CH | piperazine | —CO—CH₂— | 4 | H | — | — |
| 14 | CH₃ | Cl | CH | piperazine | —CO—CH₂— | 4 | H | Chl | 100 |
| 15 | CH₃ | Cl | CH | piperazine | —CO—CH₂—O— | 4 | H | — | — |
| 16 | CH₃ | Cl | CH | piperazine | —CO—CH₂—O— | 4 | H | Chl | 100 |
| 17 | H | Cl | CH | piperazine | —CO— | 4 | H | — | — |

TABLE I-continued
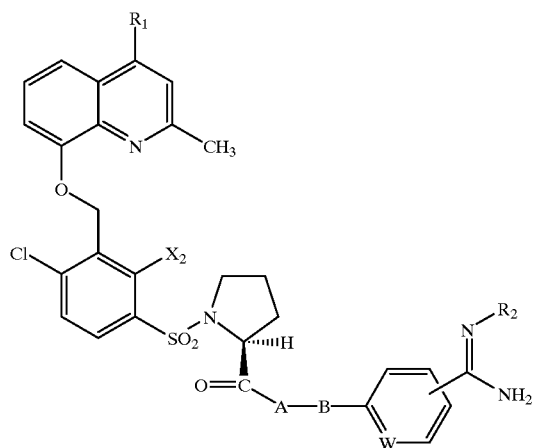
| Ex. | R₁ | X₂ | W | A | B | Pos. (a) | R₂ | Salt (b) | Activity (%) |
|---|---|---|---|---|---|---|---|---|---|
| 18 | H | Cl | CH | -N(piperazine)N- | —CO— | 4 | H | Chl | 100 |
| 19 | H | Cl | CH | -N(piperazine)N- | —CO—CH₂— | 4 | H | — | — |
| 20 | H | Cl | CH | -N(piperazine)N- | —CO—CH₂— | 4 | H | Chl | 100 |
| 21 | H | Cl | CH | -N(piperazine)N- | —CO—CH₂—O— | 4 | H | — | — |
| 22 | H | Cl | CH | -N(piperazine)N- | —CO—CH₂—O— | 4 | H | Chl | 100 |
| 23 | H | Cl | CH | —NH-(piperidine)-N— | —CO— | 4 | H | — | — |
| 24 | H | Cl | CH | —NH-(piperidine)-N— | —CO— | 4 | H | Ms | 98.9 |
| 25 | CH₃ | Cl | CH | —NH-(piperidine)-N— | —CO— | 4 | H | — | — |
| 26 | CH₃ | Cl | CH | —NH-(piperidine)-N— | —CO— | 4 | H | Ms | 100 |

TABLE I-continued

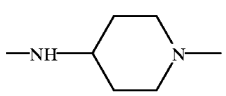

| Ex. | R₁ | X₂ | W | A | B | Pos. (a) | R₂ | Salt (b) | Activity (%) |
|---|---|---|---|---|---|---|---|---|---|
| 27 | CH₃ | Cl | CH | —NH—[1-methylpiperidin-4-yl] | —CO—CH₂—O— | 4 | H | — | — |
| 28 | CH₃ | Cl | CH | —NH—[1-methylpiperidin-4-yl] | —CO—CH₂—O— | 4 | H | Ms | 98 |
| 29 | CH₃ | Cl | CH | —NH—CH₂—[1-methylpiperidin-4-yl] | —CO—CH₂—O— | 4 | H | — | — |
| 30 | CH₃ | Cl | CH | —NH—CH₂—[1-methylpiperidin-4-yl] | —CO—CH₂—O— | 4 | H | Ms | 99.3 |
| 31 | CH₃ | Cl | CH | —NH—CH₂—[1-methylpiperidin-4-yl] | —CO—CH₂— | 4 | H | — | — |
| 32 | CH₃ | Cl | CH | —NH—CH₂—[1-methylpiperidin-4-yl] | —CO—CH₂— | 4 | H | Chl | — |
| 33 | CH₂ | Cl | CH | —NH—CH₂—[1-methylpiperidin-4-yl] | —CO— | 4 | H | — | — |
| 34 | CH₃ | Cl | CH | —NH—CH₂—[1-methylpiperidin-4-yl] | —CO— | 4 | H | Chl | — |
| 35 | H | Cl | CH | —NH—CH₂—[1-methylpiperidin-4-yl] | —CO— | 4 | H | Chl | — |

TABLE I-continued

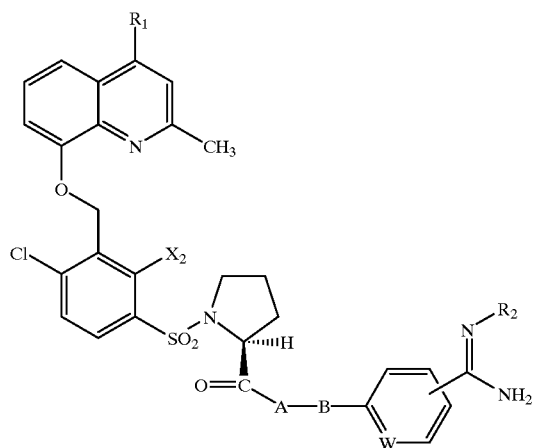

| Ex. | $R_1$ | $X_2$ | W | A | B | Pos. (a) | $R_2$ | Salt (b) | Activity (%) |
|---|---|---|---|---|---|---|---|---|---|
| 36 | H | Cl | CH | —NH—CH$_2$—(1-methylpiperidin-4-yl) | —CO—CH$_2$— | 4 | H | — | — |
| 37 | H | Cl | CH | —NH—CH$_2$—(1-methylpiperidin-4-yl) | —CO—CH$_2$— | 4 | H | Chl | — |
| 38 | H | Cl | CH | —NH—CH$_2$—(1-methylpiperidin-4-yl) | —CO—CH$_2$—O— | 4 | H | — | — |
| 39 | H | Cl | CH | —NH—CH$_2$—(1-methylpiperidin-4-yl) | —CO—CH$_2$—O— | 4 | H | Chl | — |
| 40 | CH$_3$ | Cl | CH | —NH—(1-methylpiperidin-4-yl) | —CO—CH$_2$— | 4 | H | — | — |
| 41 | CH$_3$ | Cl | CH | —NH—(1-methylpiperidin-4-yl) | —CO—CH$_2$— | 4 | H | Chl | — |
| 42 | H | Cl | CH | —NH—(1-methylpiperidin-4-yl) | —CO—CH$_2$— | 4 | H | — | — |
| 43 | H | Cl | CH | —NH—(1-methylpiperidin-4-yl) | —CO—CH$_2$— | 4 | H | Chl | — |
| 44 | H | Cl | CH | —NH—(1-methylpiperidin-4-yl) | —CO—CH$_2$—O— | 4 | H | — | — |

TABLE I-continued

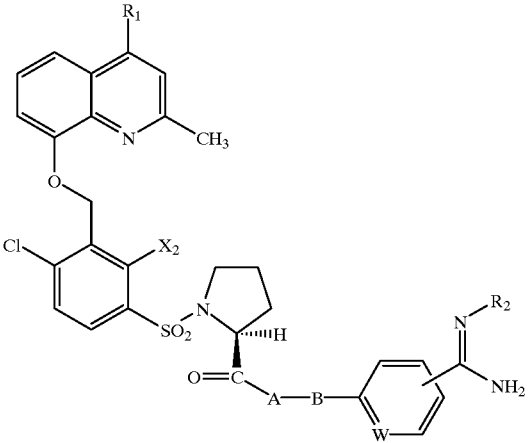

| Ex. | R₁ | X₂ | W | A | B | Pos. (a) | R₂ | Salt (b) | Activity (%) |
|---|---|---|---|---|---|---|---|---|---|
| 45 | H | Cl | CH | —NH—(N-methylpiperidin-4-yl) | —CO—CH₂—O— | 4 | H | Chl | — |
| 46 | CH₃ | Cl | CH | piperazine | —CO— | 3 | OH | — | — |
| 47 | CH₃ | Cl | CH | piperazine | —CO— | 3 | H | — | — |
| 48 | CH₃ | Cl | CH | piperazine | —CO— | 3 | H | Chl | — |
| 49 | CH₃ | Cl | CH | —NH—(CH₂)₃— | — | 4 | H | — | — |
| 50 | CH₃ | Cl | CH | —NH—(CH₂)₃— | — | 4 | H | Chl | — |
| 51 | CH₃ | Cl | CH | —NH—(CH₂)₂— | — | 4 | H | Chl | — |
| 52 | CH₃ | Cl | CH | piperazine | —CO— | 4 | H | — | — |
| 53 | CH₃ | Cl | CH | piperazine | —CO— | 4 | H | — | — |
| 54 | CH₃ | Cl | CH | piperazine | —CO—CH=CH— | 4 | OH | — | — |
| 55 | CH₃ | Cl | CH | piperazine | —CO—CH=CH— | 4 | H | — | — |
| 56 | CH₃ | OCH₃ | CH | piperazine | —CO— | 4 | OH | — | — |

TABLE I-continued
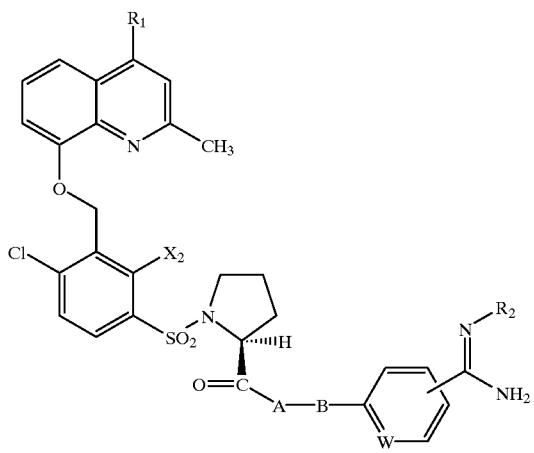
| Ex. | $R_1$ | $X_2$ | W | A | B | Pos. (a) | $R_2$ | Salt (b) | Activity (%) |
|---|---|---|---|---|---|---|---|---|---|
| 57 | $CH_3$ | $OCH_3$ | CH | piperazine | —CO— | 4 | H | — | — |
| 58 | $CH_3$ | $OCH_3$ | CH | piperazine | —CO— | 4 | H | Chl | — |
| 59 | $CF_3$ | Cl | CH | piperazine | —CO— | 4 | OH | — | — |
| 60 | $CF_3$ | Cl | CH | piperazine | —CO— | 4 | H | — | — |
| 61 | $CF_3$ | Cl | CH | piperazine | —CO— | 4 | H | Ms | — |
| 62 | $CH_3$ | Cl | CH | piperazine | —$SO_2$— | 4 | OH | — | — |
| 63 | $CH_3$ | Cl | CH | piperazine | —$SO_2$— | 4 | H | — | — |

TABLE I-continued

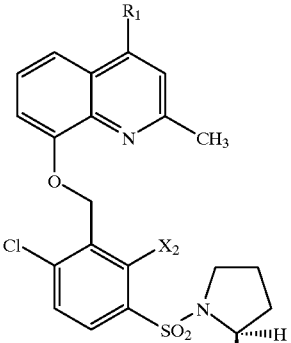

| Ex. | $R_1$ | $X_2$ | W | A | B | Pos. (a) | $R_2$ | Salt (b) | Activity (%) |
|---|---|---|---|---|---|---|---|---|---|
| 64 | $CH_3$ | Cl | CH | 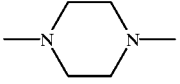 piperazine | —$SO_2$— | 4 | H | Chl | — |
| 65 | $CH_3$ | Cl | N | —NH—$CH_2$— | — | 5* | H | — | — |
| 66 | $CH_3$ | Cl | N | —NH—$CH_2$— | — | 5* | H | Chl | — |
| 67 | $CH_3$ | Cl | N | 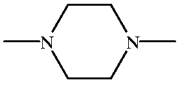 piperazine | —CO— | 5* | OH | — | — |
| 68 | $CH_3$ | Cl | N | 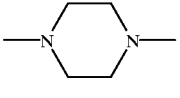 piperazine | —CO— | 5* | H | — | — |
| 69 | $CH_3$ | Cl | N | piperazine | —CO— | 5* | H | Ms | — |
| 70 | $CH_3$ | Cl | CH | 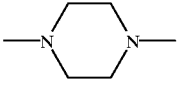 piperazine | —CO— | 4 | OH | — | — |

Notes (a) position of the amidine group on the aromatic ring

*position relative to the nitrogen of the pyridinyl group (b) Chl: salt with hydrochloric acid Ms: salt with methanesulfonic acid

We claim:

1. A compound derived from N-benzenesulfonyl-(L)-proline, wherein said compound is selected from the group consisting of:

(i) a compound of formula I

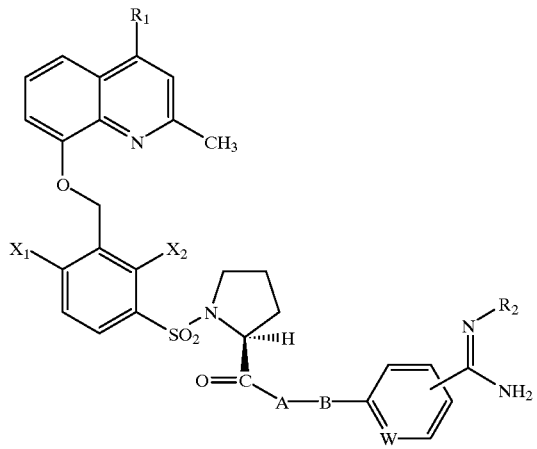

(I)

in which:

$X_1$ and $X_2$ are each independently a halogen atom or a $C_1$–$C_3$-alkoxy group, $R_1$ is a hydrogen atom, a $C_1$–$C_3$-trifluoroalkyl group or a $C_1$–$C_3$-alkyl group with a linear or branched hydrocarbon chain, $R_2$ is a hydrogen atom or an OH group, A is a group

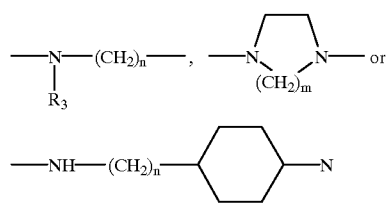

B is a single bond, —CO—, —CO—CH$_2$—, —CO—CH$_2$—O—, CO—CH=CH— or —SO$_2$—, m is 2 or 3, n is 0, 1, 2 or 3, $R_3$ is a hydrogen atom or a methyl group, and W is CH or N, the amidine group C(=NR$_2$)NH$_2$ being in the 2-, 3- or 4-position on the aromatic ring; and (ii) its addition salts.

2. The compound according to claim 1, wherein $X_1$ and $X_2$ in formula 1 are each a chlorine atom.

3. A process for producing a compound of formula I of claim 1, comprising the steps of:

1) reacting an acid of formula II

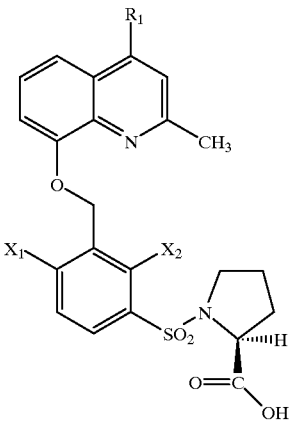

(II)

in which:

$R_1$ is a hydrogen atom, a trifluoromethyl group or a $C_1$–$C_3$-alkyl group with a linear or branched hydrocarbon chain, and $X_1$ and $X_2$ are each independently a halogen or a $C_1$–$C_3$-alkoxy group, with an amine of formula III

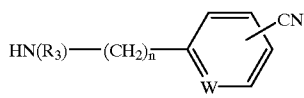

(III)

in which $R_3$ is a hydrogen atom or a methyl group, n is 0, 1, 2 or 3, and W is CH or N.

in a solvent, in the presence of activators to create peptide bonds, at a temperature close to room temperature, for 2 to 50 hours, to give a compound of formula IV

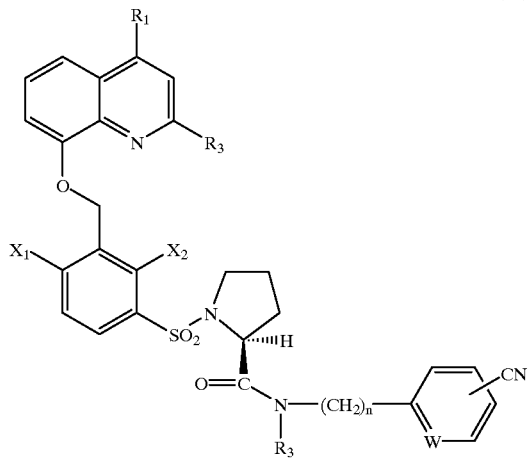

(IV)

in which $R_1$, $R_3$, $X_1$, $X_2$, n and W are as defined above;

2) reacting the resulting compound of formula IV with excess hydrogen sulfide, in an anhydrous solvent, in the presence of triethylamine, at a temperature between 0 and 40° C., for 2 to 40 hours, to give a compound of formula V

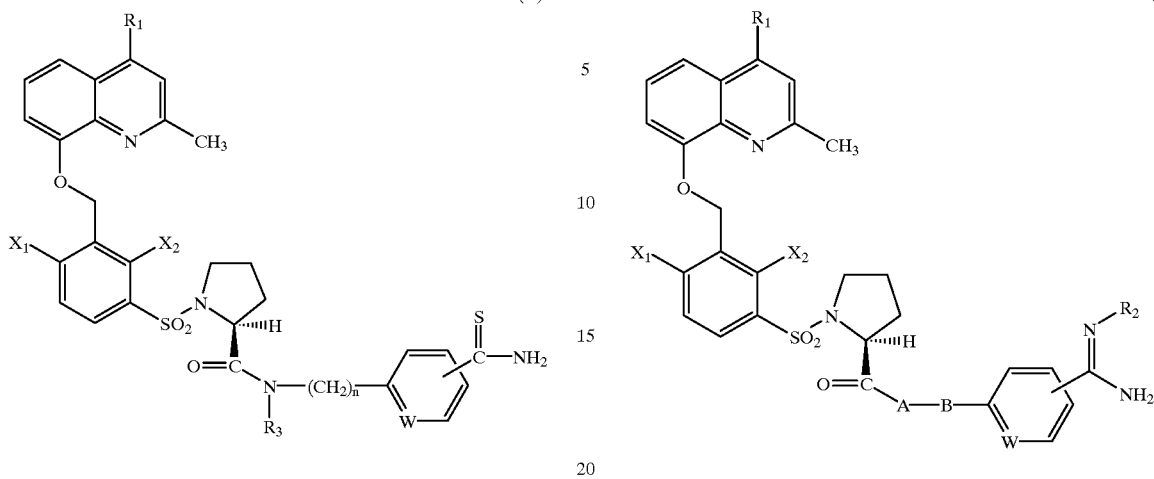

in which $R_1$, $R_3$, $X_1$, $X_2$, n and W are as defined above;

3) reacting the resulting compound of formula V with an excess of a methylating agent, in a solvent, at a temperature close to the boiling point of the reaction medium for 1 to 5 hours, to give a compound of formula VI

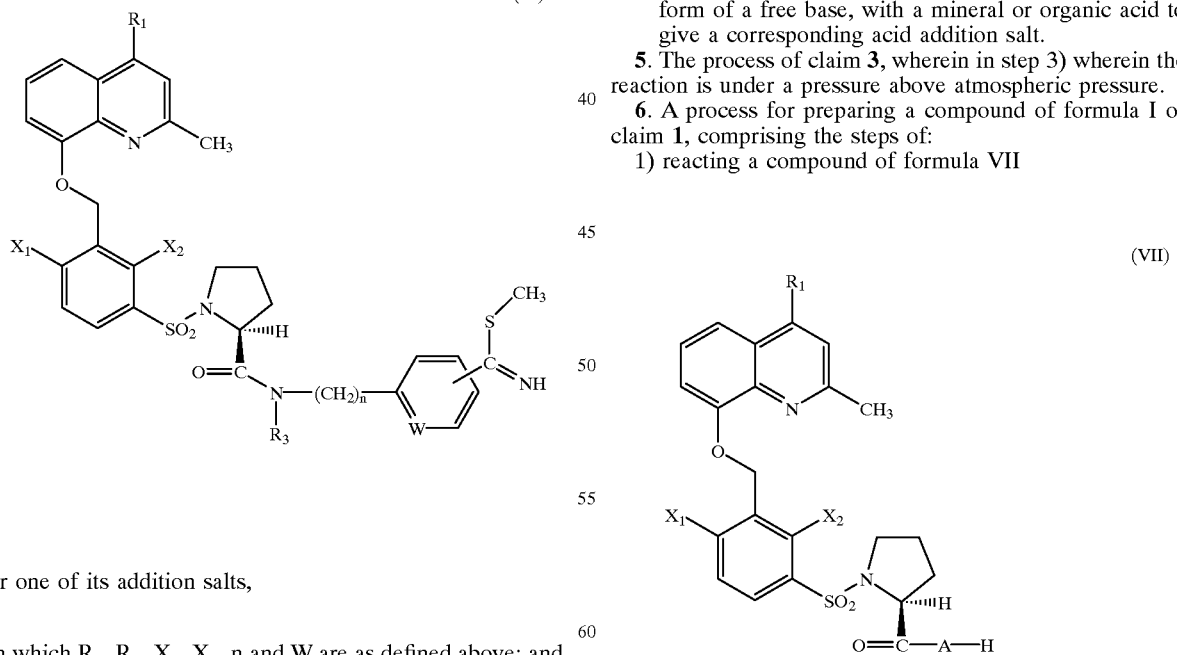

or one of its addition salts, in which $R_1$, $R_3$, $X_1$, $X_2$, n and W are as defined above; and 4) reacting the resulting compound of formula VI with an ammonium salt, in a solvent, at a temperature between room temperature and 100° C., for 1 to 10 hours, to give a compound of formula I:

in which:
$R_1$ is a hydrogen atom, a trifluoromethyl group or a $C_1$–$C_3$-alkyl group with a linear or branched hydrocarbon chain,
$X_1$ and $X_2$ are each independently a halogen atom or a $C_1$–$C_3$-alkyl group,
A is a group —N($R_3$)—$(CH_2)_n$—,
B is a single bond,
W is CH or N,
$R_2$ is a hydrogen atom,
$R_3$ is H or $CH_3$, and
n is 0, 1, 2 or 3.

4. The process of claim 3, further comprising the step of:
5) reacting the resulting compound of formula I, in the form of a free base, with a mineral or organic acid to give a corresponding acid addition salt.

5. The process of claim 3, wherein in step 3) wherein the reaction is under a pressure above atmospheric pressure.

6. A process for preparing a compound of formula I of claim 1, comprising the steps of:
1) reacting a compound of formula VII in which:
$R_1$ is a hydrogen atom, a trifluoromethyl group or a $C_1$–$C_3$-alkyl group with a linear or branched hydrocarbon chain, $X_1$ and $X_2$ are each independently a halogen or a methoxy group, and A is a group

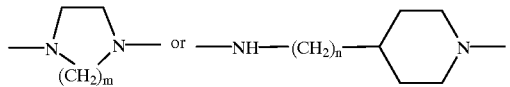

in which n is 0, 1, 2 or 3, and m is 2 or 3,
with a compound of formula VIII:

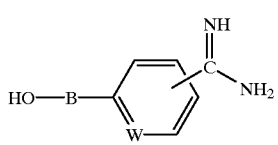

in which B is —CO—, —CO—CH$_2$—, —CO—CH$_2$—O—, or CO—CH=CH—, in a solvent, in the presence of activators to create peptide bonds, at a temperature close to room temperature, for 2 to 50 hours, to give a compound of formula I

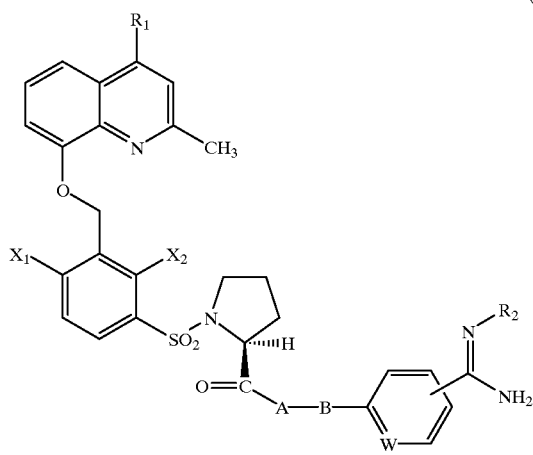

in which $R_1$, $X_1$ and $X_2$ are as defined above,
A is a group

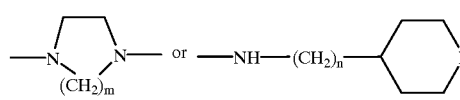

B is a group —CO—, —CO—CH$_2$—, —CO—CH$_2$—O—, or CO—CH=CH—,
m is 2 or 3, n is 0, 1, 2, or 3
W is CH, and
$R_2$ is a hydrogen atom.

7. The process of claim 6, further comprising the step of:
2) reacting the resulting compound of formula I with an acid to give a corresponding acid addition salt.

8. A process for preparing a compound of formula I of claim 1, comprising the steps of:
1) reacting a compound of formula VII

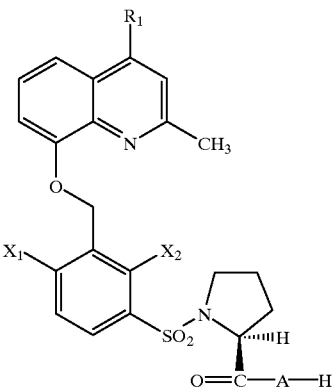

in which:

$R_1$ is a hydrogen atom, a trifluoromethyl group or a $C_1$–$C_3$-alkyl group with a linear or branched hydrocarbon chain, $X_1$ and $X_2$ are each independently a halogen or a methoxy group, and A is a group

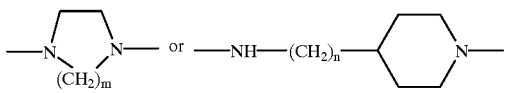

in which m is 2 or 3, and n is 0, 1, 2 or 3,
with a compound of formula IX

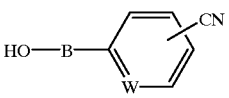

in which B is —CO—, —CO—CH$_2$—, —CO—CH$_2$—O—, or CO—CH=CH—, and W is CH or N,
in a solvent, in the presence of activators to create peptide bonds, at a temperature close to room temperature, for 2 to 50 hours, to give a compound of formula X

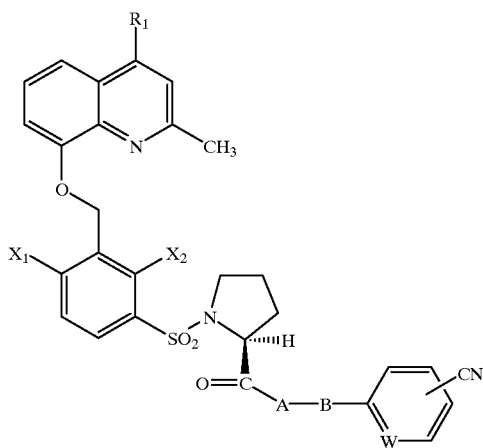

(X)

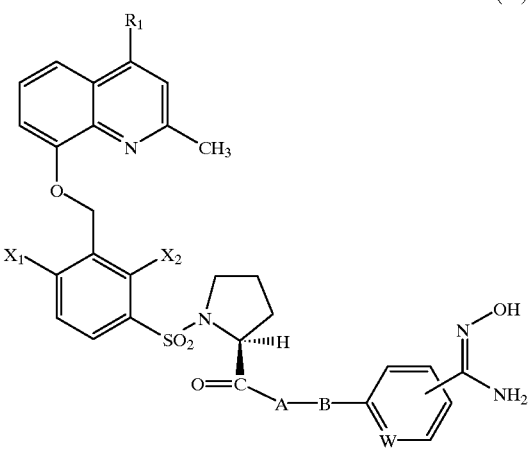

(XI)

in which $R_1$, $X_1$ and $X_2$, A, B and W are as defined in the starting compounds;

2) reacting the resulting compound of formula X with hydroxylamine, in a solvent, at room temperature, for 1 to 12 hours, to give the compound of formula XI in which $R_1$, $X_1$ and $X_2$, A, B and W are as defined in the starting compounds;

3) reacting the resulting compound of formula XI with acetic anhydride, at room temperature, for 1 to 8 hours, to give the compound of formula XII

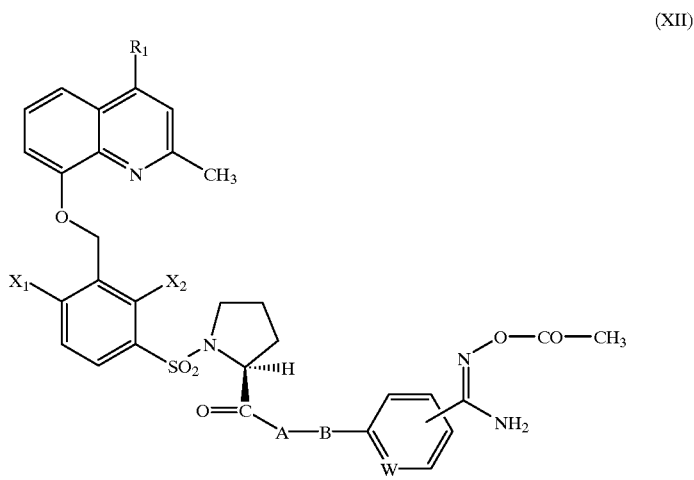

(XII)

in which $R_1$, $X_1$ and $X_2$, A, B and W are as defined in the starting compounds;

4) reducing the resulting compound of formula XII by catalytic hydrogenation in the presence of a catalyst, in a solvent, under a hydrogen pressure of about $10^5$ to $10^6$ pascals, at room temperature, to give the compound of formula I

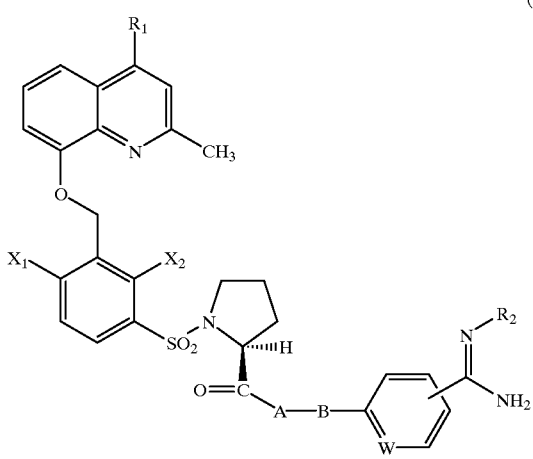
(I)

in which $R_1$, $X_1$ and $X_2$, A, B and W are as defined in the starting compounds and $R_2$ is a hydrogen atom.

9. The process of claim 8, further comprising the step of:

5) reacting the resulting compound of formula I with an acid to give a corresponding acid addition salt.

10. The process of claim 9, wherein in step 3) the reaction is carried out in a solvent.

11. A therapeutic composition for treatment and/or prevention of a pathological condition mediated by bradykinin in a patient in need of such treatment or prevention, comprising:
a physiologically acceptable excipient, and
at least an effective bradykinin inhibiting amount of a compound selected from the group consisting of a compound of formula I or its non-toxic addition salt according to claim 1.

12. A pharmacological composition comprising an effective bradykinin inhibiting amount of a compound of formula I or one of its addition salts according to claim 1, and at least one pharmaceutical carrier or diluent.

13. A method for treating or preventing a pathological condition mediated by bradykinin in a patient in need of such treatment or prevention by administering to said patient a bradykinin antagonistic effective amount of compound of formula I or one of its non-toxic addition salts according to claim 1.

14. The method of claim 13, wherein the pathological condition involves pain.

15. The method of claim 13, wherein the pathological condition involves inflammation.

16. The method of claim 13, wherein the pathological condition is meningitis or cerebrovascular complications caused by cerebral traumatic shock.

17. The method of claim 13, wherein the pathological condition results from cerebral traumatic shock.

* * * * *